US011747303B2

(12) United States Patent
Iwasaki et al.

(10) Patent No.: US 11,747,303 B2
(45) Date of Patent: Sep. 5, 2023

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Tokyo (JP); Satoshi Shirotori, Kanagawa (JP); Akira Kikitsu, Kanagawa (JP); Yoshihiro Higashi, Ishikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 91 days.

(21) Appl. No.: 17/395,183

(22) Filed: Aug. 5, 2021

(65) Prior Publication Data

US 2022/0187247 A1 Jun. 16, 2022

(30) Foreign Application Priority Data

Dec. 14, 2020 (JP) ................................ 2020-206822

(51) Int. Cl.
*G01N 27/90* (2021.01)
*G01N 33/2045* (2019.01)

(52) U.S. Cl.
CPC ..... *G01N 27/9006* (2013.01); *G01N 33/2045* (2019.01)

(58) Field of Classification Search
CPC .................................................... G01R 33/093
See application file for complete search history.

(56) References Cited

U.S. PATENT DOCUMENTS

2006/0072249 A1* 4/2006 Wakui .................. G11B 5/3903 257/E27.005
2010/0045285 A1* 2/2010 Ohmori ................ G01R 33/093 427/547
2018/0271395 A1* 9/2018 Iwasaki .................... A61B 5/24
2019/0293735 A1 9/2019 Ushioda et al.

FOREIGN PATENT DOCUMENTS

JP 2018-155719 10/2018
WO WO 2017/204151 A1 11/2017

* cited by examiner

*Primary Examiner* — Jas A Sanghera
(74) *Attorney, Agent, or Firm* — Finnegan, Henderson, Farabow, Garrett & Dunner, LLP

(57) ABSTRACT

According to one embodiment of the invention, a magnetic sensor includes a first sensor part. The first sensor part includes a first magnetic member, a first counter magnetic member, and a first magnetic element. A direction from the first magnetic member to the first counter magnetic member is along a first direction. The first magnetic element includes one or a plurality of first extending portions. A first portion of the first extending portion overlaps the first magnetic member in a second direction crossing the first direction. A first counter portion of the first extending portion overlaps the first counter magnetic member in the second direction. A first direction length along the first direction of the first extending portion is longer than a third direction length along a third direction of the first extending portion. The third direction crosses a plane including the first direction and the second direction.

20 Claims, 18 Drawing Sheets

MAGNETIC SENSOR AND INSPECTION DEVICE

CROSS-REFERENCE TO RELATED APPLICATIONS

This application is based upon and claims the benefit of priority from Japanese Patent Application No. 2020-206822, filed on Dec. 14, 2020; the entire contents of which are incorporated herein by reference.

FIELD

Embodiments of the invention relate generally to a magnetic sensor and an inspection device.

BACKGROUND

There is a magnetic sensor using on a magnetic layer. There is an inspection device using the magnetic sensor. It is desired to improve the sensitivity of the magnetic sensor.

DETAILED DESCRIPTION

Figure 1A:
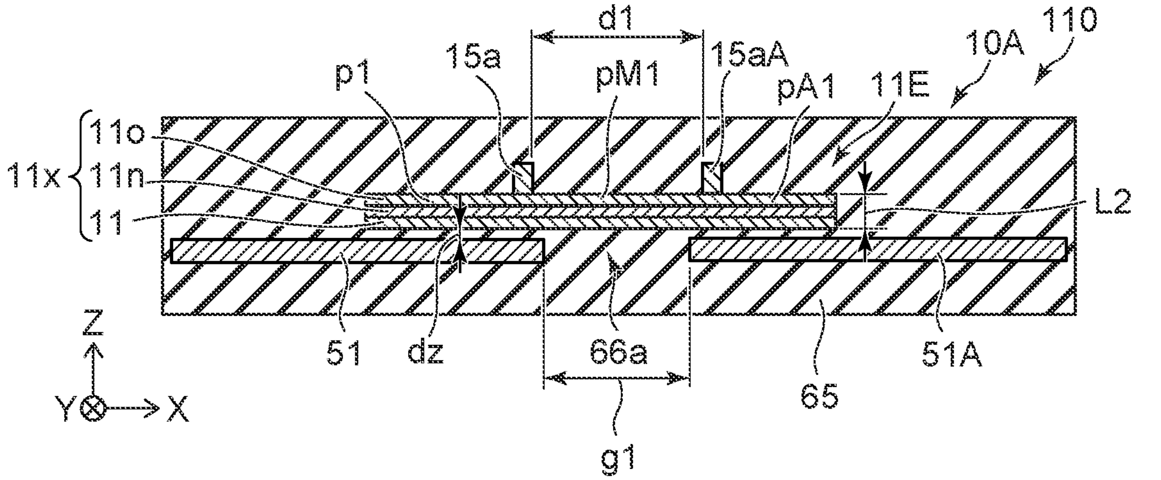
FIGS. 1A and 1B are schematic views illustrating a magnetic sensor according to a first embodiment.

According to one embodiment of the invention, a magnetic sensor includes a first sensor part. The first sensor part includes a first magnetic member, a first counter magnetic member, and a first magnetic element. A direction from the first magnetic member to the first counter magnetic member is along a first direction. The first magnetic element includes one or a plurality of first extending portions. A first portion of the first extending portion overlaps the first magnetic member in a second direction crossing the first direction. A first counter portion of the first extending portion overlaps the first counter magnetic member in the second direction. A first direction length along the first direction of the first extending portion is longer than a third direction length along a third direction of the first extending portion. The third direction crosses a plane including the first direction and the second direction.

According to one embodiment, an inspection device includes the above magnetic sensor, and a processor configured to process a signal output from the magnetic sensor.

Various embodiments of the invention are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
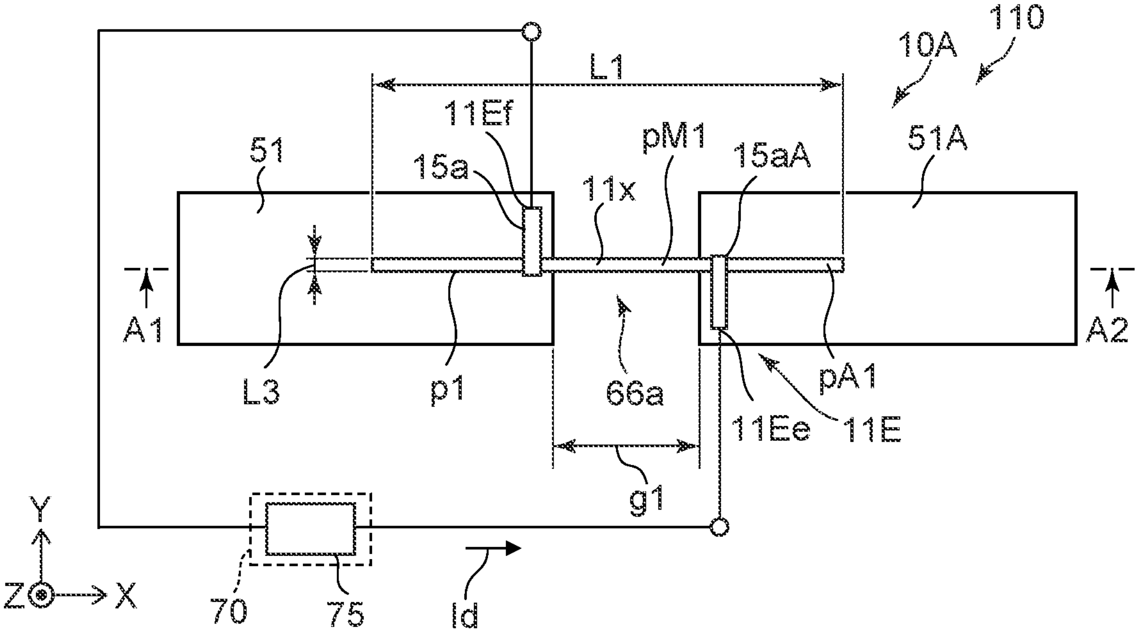

FIGS. 1A and 1B are schematic views illustrating a magnetic sensor according to a first embodiment.

FIG. 1A is a cross-sectional view taken along line A1-A2 of FIG. 1B. FIG. 1B is a plan view.

As shown in FIGS. 1A and 1B, a magnetic sensor 110 according to the embodiment includes a first sensor part 10A. The first sensor part 10A includes a first magnetic member 51, a first counter magnetic member 51A, and a first magnetic element 11E. The first magnetic element 11E is, for example, a magneto resistance element.

The direction from the first magnetic member 51 to the first counter magnetic member 51A is along the first direction. The first direction is the Z-axis direction. One direction perpendicular to the Z-axis direction is defined as the X-axis direction. The direction perpendicular to the Z-axis direction and the X-axis direction is defined as the Y-axis direction.

The first magnetic element 11E includes a first extending portion 11*x*. The first extending portion 11*x* extends along the first direction (X-axis direction). The first magnetic element 11E may include one or more first extending portions 11*x*. In this example, the number of first extending portions 11*x* is 1. An example in which a plurality of first extending portions 11*x* are provided will be described later.

As shown in FIG. 1A, the first extending portion 11*x* includes a first magnetic layer 11, a first counter magnetic layer 11*o*, and a first nonmagnetic layer 11*n*. The first nonmagnetic layer 11*n* is provided between the first magnetic layer 11 and the first counter magnetic layer 11*o*.

For example, at least one of the first magnetic layer 11 and the first counter magnetic layer 11*o* includes at least one selected from the group consisting of Fe, Co, and Ni. These magnetic layers are, for example, ferromagnetic layers. An example of the material of the magnetic layer will be described later. The first nonmagnetic layer 11*n* is, for example, conductive. The first nonmagnetic layer 11*n* includes, for example, Cu. The first magnetic element 11E is, for example, a GMR (Giant magneto resistance) element.

The electrical resistance of the first magnetic element 11E changes according to the magnetic field applied to the first magnetic element 11E. When the magnetic field to be detected is applied to the first magnetic element 11E, a direction of magnetization of at least one of the first magnetic layer 11 and the first counter magnetic layer 11*o* changes. As a result, an angle between the direction of magnetization of the first magnetic layer 11 and the direction of magnetization of the first counter magnetic layer 11*o* changes. The electric resistance of the first magnetic element 11E changes according to the change in the angle. The change in electrical resistance is based, for example, on the magneto resistance effect.

As shown in FIG. 1A, the first extending portion 11*x* includes a first portion p1 and a first counter portion pA1. The first portion p1 overlaps the first magnetic member 51 in the second direction. The second direction crosses the first direction. The second direction is, for example, the Z-axis direction. The first counter portion pA1 of the first extending portion 11*x* overlaps the first counter magnetic member 51A in the second direction (Z-axis direction).

For example, the magnetic field to be inspected is collected by the first magnetic member 51 and the first counter magnetic member 51A. The collected magnetic field is efficiently applied to the first magnetic element 11E. As a result, high sensitivity can be obtained. The first magnetic member 51 and the first counter magnetic member 51A function as, for example, an MFC (Magnetic Field Concentrator).

As shown in FIGS. 1A and 1B, the first extending portion 11*x* includes a first intermediate portion pM1 between the first portion p1 and the first counter portion pA1. The first intermediate portion pM1 overlaps a region 66*a* between the first magnetic member 51 and the first counter magnetic member 51A in the second direction (Z-axis direction). For example, the insulating member 65 may be provided around the first magnetic element 11E, the first magnetic member 51, and the first counter magnetic member 51A. The region 66*a* may be a part of the insulating member 65. In FIG. 1B, the insulating member 65 is omitted.

As shown in FIG. 1B, the first extending portion 11*x* has a first direction length L1 along the first direction (X-axis direction). The first extending portion 11*x* has a third direction length L3 along the third direction. The third direction crosses a plane including the first and second directions (e.g., the X-Z plane). The third direction is, for example, the Y-axis direction. The first direction length L1 is, for example, the length of the first extending portion 11*x*. The third direction length L3 is, for example, the width of the first extending portion 11*x*. In the embodiment, the first direction length L1 is longer than the third direction length L3.

For example, a current flowing along the X-axis direction is supplied to the first magnetic element 11E, and the electric resistance of the first magnetic element 11E is detected.

For example, as shown in FIGS. 1A and 1B, the first magnetic element 11E further includes a first electrode 15*a* and a first counter electrode 15*a*A. The first electrode 15*a* is electrically connected to the first portion p1. The first electrode 15*a* overlaps the first magnetic member 51 in the second direction (Z-axis direction). The first counter electrode 15*a*A is electrically connected to the first counter portion pA1. The first counter electrode 15*a*A overlaps the first counter magnetic member 51A in the second direction (Z-axis direction). The direction from the first electrode 15*a* to the first counter electrode 15*a*A is along the X-axis direction.

As shown in FIG. 1B, for example, the first electrode 15*a* and the first counter electrode 15*a*A are electrically connected to an element current circuit 75. The element current circuit 75 can supply the element current Id to the first extending portion 11*x* of the first magnetic element 11E via the first electrode 15*a* and the first counter electrode 15*a*A. The change in the electric resistance of the first magnetic element 11E is detected by the element current Id. The first counter electrode 15*a*A corresponds to one end 11Ee of the first magnetic element 11E. The first electrode 15*a* corresponds to the other end 11Ef of the first magnetic element 11E. The element current circuit 75 may be included in a control circuit part 70.

In the embodiment, the electrical resistance of the first intermediate portion pM1 of the first extending portion 11*x* is detected. The magnetic field collected by the first magnetic member 51 and the first counter magnetic member 51A is efficiently applied to the first intermediate portion pM1. Further, the first portion p1 and the first counter portion pA1 on the outer side of the detection target of the electric resistance overlap the first magnetic member 51 and the first counter magnetic member 51A, thereby the electrical resistance of the intermediate portion pM1 in the middle portion of the first extending portion lix changes more efficiently. According to the embodiment, it is possible to provide a magnetic sensor which is possible to improve the sensitivity.

In the embodiment, the first direction length L1 is, for example, not less than 5 μm and not more than 1000 μm. The third direction length L3 is, for example, not less than 1 μm and not more than 20 μm. As shown in FIG. 1A, the first extending portion 11*x* has a second direction length L2 along the second direction (Z-axis direction). The second direction length L2 is, for example, a thickness. In the embodiment, the second direction length L2 is, for example, not less than 0.01 μm and not more than 0.1 μm.

A distance g1 between the first magnetic member 51 and the first counter magnetic member 51A along the X-axis direction is, for example, not less than 1 μm and not more than 10 μm.

For example, a distance d1 between the first electrode 15*a* and the first counter electrode 15*a*A (see FIG. 1A) is greater than or equal to the distance g1. When the distance d1 is the distance g1 or more, for example, the change in the electrical resistance of the first extending portion 11*x* becomes large. High efficiency is easily obtained.

For example, the first electrode 15*a* and the first counter electrode 15*a*A do not overlap the region 66*a* between the first magnetic member 51 and the first counter magnetic member 51A in the second direction (Z-axis direction).

The first portion p1 may include, for example, a portion that does not overlap the first electrode 15*a* in the second direction (Z-axis direction). The first counter portion pA1 may include a portion that does not overlap the first counter electrode 15*a*A in the second direction. The length of the first extending portion 11*x* along the X-axis direction may be longer than the length along the X-axis direction of the region where the first electrode 15*a* and the first counter electrode 15*a*A are provided. Since the first extending portion 11*x* is long, for example, the first intermediate portion pM1 is continuous with the first portion p1 or the first counter portion pA1. Since the first intermediate portion pM1 has no end portion in the X-axis direction, the influence of the generation of magnetic domains at the end portion does not occur. As a result, the change in the electric resistance of the first intermediate portion pM1 is stabilized, and noise is reduced.

As shown in FIG. 1A, in one example, in the second direction (Z-axis direction), at least a part of the first portion p1 is between the first magnetic member 51 and the first electrode 15*a*. In the second direction, at least a part of the first counter portion pA1 is between the first counter magnetic member 51A and the first counter electrode 15*a*A.

An example of the simulation result of the characteristics of the magnetic sensor will be described below.

Figure 2:
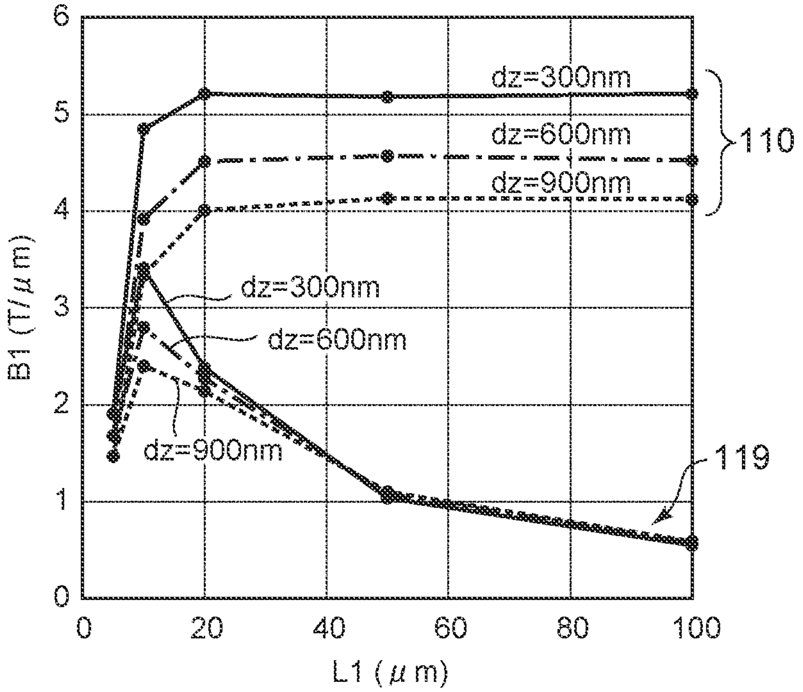
FIG. 2 is a graph illustrating characteristics of the magnetic sensor.

FIG. 2 is a graph illustrating characteristics of the magnetic sensor.

FIG. 2 illustrates the characteristics of the magnetic sensor 110 and the characteristics of a magnetic sensor 119 of the reference example. In the magnetic sensor 119 of the reference example, the extending portion of the first magnetic element 11E has a band shape along the Y-axis direction. In the magnetic sensor 119, a current flows in the GMR element along the Y-axis direction. In the magnetic sensor 119, a current flows along the Y-axis direction in the entire region of the width (length along the X-axis direction) of the GMR element. In the magnetic sensor 119, the detection output is determined by the amount of magnetic flux applied to the entire band-shaped region along the Y-axis direction. In the magnetic sensor 119, the amount of magnetic flux averaged in the region of the extending portion extending along the Y-axis direction corresponds to the output.

In the magnetic sensor 110, the first portion p1 of the first extending portion 11*x* overlaps the first magnetic member 51, and the first counter portion pA1 overlaps the first counter magnetic member 51A. The first extending portion 11*x* has a band shape along the X-axis direction. In the magnetic sensor 110, a current flows in a region between two electrodes of the first extending portion 11*x* extending in the X-axis direction. In the magnetic sensor 110, the amount of magnetic flux averaged in the region between the two electrodes corresponds to the output. The amount of magnetic flux corresponds to the sensitivity.

In the simulation model shown in FIG. 2, the distance g1 between the first magnetic member 51 and the first counter magnetic member 51A along the X-axis direction is 5 μm. In the magnetic sensor 110, the distance d1 between the two electrodes along the X-axis direction is 5 μm. The length (thickness) of each of the first magnetic member 51 and the first counter magnetic member 51A along the Z-axis direction is 5 μm. The specific magnetic permeability of the stacked body including the first magnetic layer 11, the first nonmagnetic layer 11*n*, and the first counter magnetic layer 11*o* is 2000. The distance dz (see FIG. 1A) along the Z-axis direction between the first magnetic member 51 and the first magnetic layer 11 is the same as the distance along the Z-axis direction between the first counter magnetic member 51A and the first magnetic layer 11. In the simulation, the distance dz is 300 nm, 600 nm, or 900 nm.

In the simulation, in the magnetic sensor 110, the first direction length L1 of the first extending portion 11*x* along the X-axis direction is changed. In the magnetic sensor 119, the first direction length L1 of the extending portion along the Y-axis direction along the X-axis direction is changed. In the magnetic sensor 119, the first direction length L1 corresponds to the width along the X-axis direction.

The horizontal axis of FIG. 2 is the first direction length L1. The vertical axis of FIG. 2 is the magnetic flux amount B1. As shown in FIG. 2, when the first direction length L1 is 5 μm, there is no clear difference in the magnetic flux amount of B1 between the magnetic sensor 110 and the magnetic sensor 119. When the first direction length L1 is 10 μm, the magnetic flux amount B1 in the magnetic sensor 110 is significantly larger than the magnetic flux amount B1 in the magnetic sensor 119.

In the magnetic sensor 119, the magnetic flux amount B1 decreases when the first direction length L1 exceeds 10 μm. In the magnetic sensor 110, the magnetic flux amount B1 clearly increases in a region where the first direction length L1 is 20 μm or less. In the magnetic sensor 110, a large magnetic flux amount B1 is maintained in a region where the first direction length L1 exceeds 20 μm.

As shown in FIG. 2, the magnetic flux amount B1 corresponding to the sensitivity of the magnetic sensor 110 is larger than the magnetic flux amount B1 corresponding to the sensitivity of the magnetic sensor 119. As described above, when the first direction length L1 is longer than the distance g1, high sensitivity can be obtained. As described already, in the magnetic sensor 110, since the first intermediate portion pM1 has no end portion in the X-axis direction, magnetic noise can be reduced. The distance dz is, for example, not less than 10 nm and not more than 1000 nm. When the distance dz is not less than 10 nm, for example, electrical insulation between the first extending portion 11*x* and the first magnetic member 51 can be stably obtained. When the distance dz is not more than 1000 nm, a large magnetic flux amount B1 can be easily obtained.

Figure 3A:
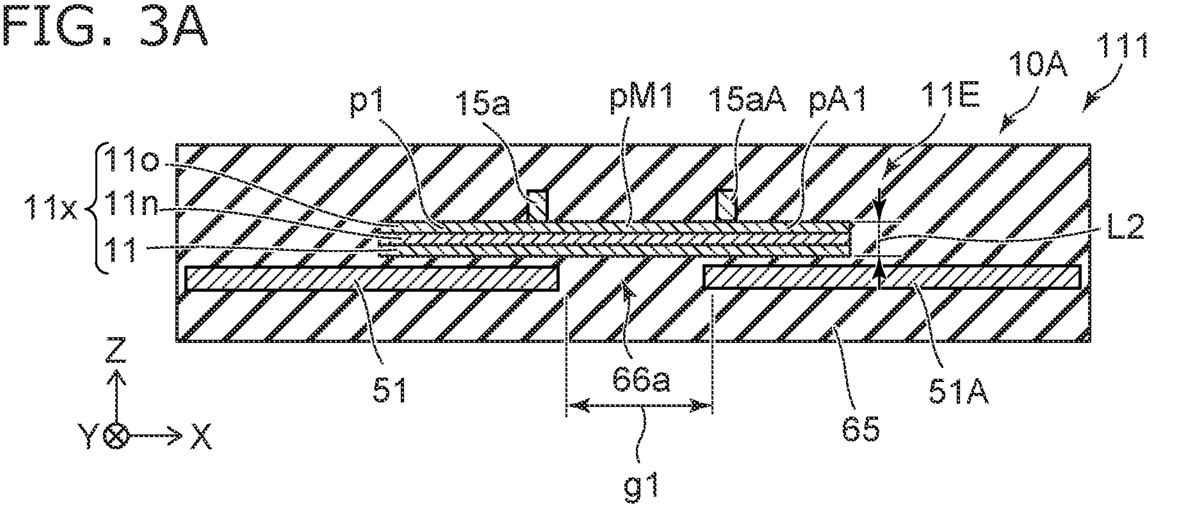
FIGS. 3A and 3B are schematic views illustrating a magnetic sensor according to the first embodiment.
Figure 3B:
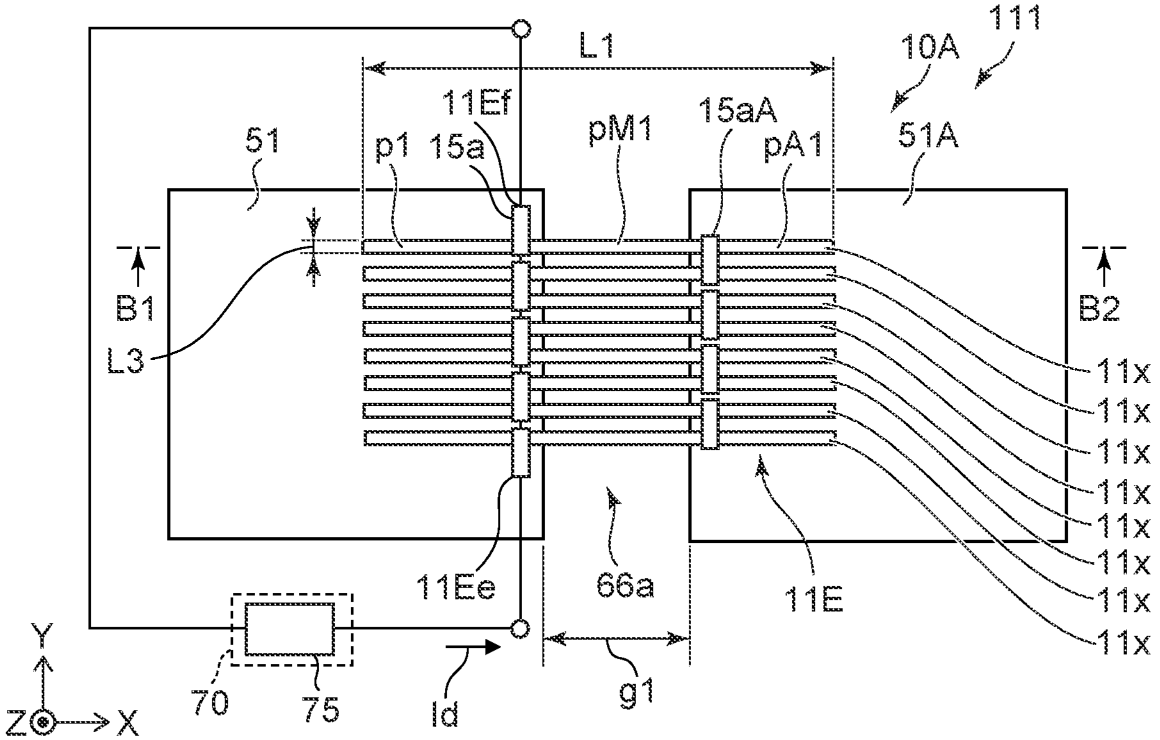

FIGS. 3A and 3B are schematic views illustrating a magnetic sensor according to the first embodiment.

FIG. 3A is a cross-sectional view taken along B1-B2 line of FIG. 3B. FIG. 3B is a plan view.

As shown in FIGS. 3A and 3B, a magnetic sensor 111 according to the embodiment includes the first sensor part 10A. The first sensor part 10A includes the first magnetic member 51, the first counter magnetic member 51A, and the first magnetic element 11E. In the magnetic sensor 111, the first magnetic element 11E includes a plurality of first extending portions 11*x*. Other configurations of the magnetic sensor 111 may be the same as the configuration of the magnetic sensor 110.

The plurality of first extending portions 11*x* are arranged along the third direction (Y-axis direction). The plurality of first extending portions 11*x* are electrically connected in a meander shape.

The first portion p1 of each of the plurality of first extending portions 11*x* overlaps the first magnetic member 51 in the Z-axis direction. The first counter portion pA1 of each of the plurality of first extending portions 11*x* overlaps the first counter magnetic member 51A in the Z-axis direction. Changes in electric resistance in each of the first intermediate portions pM1 of the plurality of first extending portions 11*x* are detected. Higher sensitivity becomes easier to be obtained.

When the plurality of first extending portions 11*x* electrically connected in a meander shape are provided, one end (electrode) of the meander-shaped conductive region becomes one end 11Ee of the first magnetic element 11E. The other end (electrode) of the meander-shaped conductive region becomes the other end 11Ef of the first magnetic element 11E.

Hereinafter, some examples of the first extending portion 11*x* will be described.

Figure 4A:
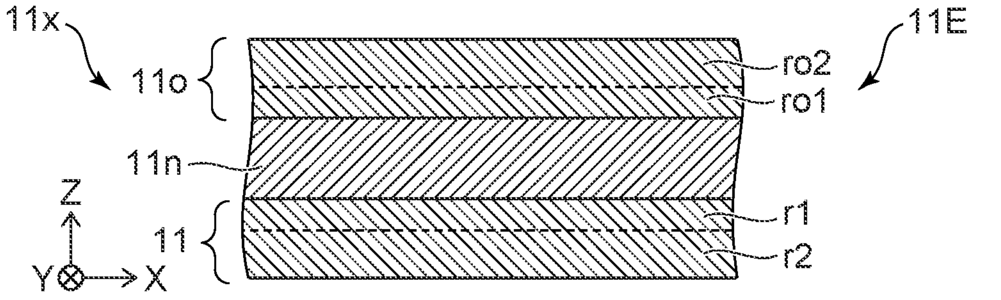
FIGS. 4A to 4C are schematic views illustrating a part of the magnetic sensor according to the first embodiment.
Figure 4B:
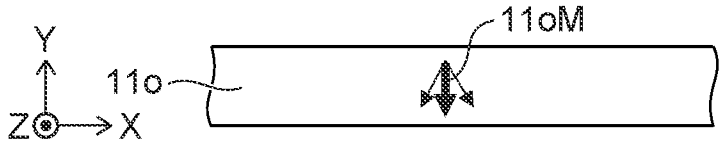
Figure 4C:
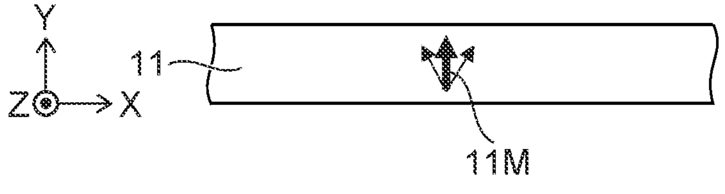

FIGS. 4A to 4C are schematic views illustrating a part of the magnetic sensor according to the first embodiment.

FIG. 4A is a cross-sectional view. FIG. 4B is a plan view of the first counter magnetic layer 11*o*. FIG. 4C is a plan view of the first magnetic layer 11. As shown in FIGS. 4B and 4C, the magnetization 11*o*M of the first counter magnetic layer 11*o* and the magnetization 11M of the first magnetic layer 11 are substantially along the third direction (Y-axis direction) in a state in which a magnetic field is not substantially applied. For example, when a magnetic field including a component in the second direction (X-axis direction) is applied to these magnetic layers, the direction of the magnetization 11*o*M and the direction of the magnetization 11M change according to the magnetic field. In this example, the first counter magnetic layer 11*o* and the first magnetic layer 11 are, for example, free magnetic layers.

The first nonmagnetic layer 11*n* includes, for example, Cu. At least one of the first magnetic layer 11 and the first counter magnetic layer 11*o* includes, for example, at least one selected from the group consisting of CoFe, CoFeNi, and NiFe. At least one of the first magnetic layer 11 and the first counter magnetic layer 11*o* may include, for example, NiFe films and CoFe films which are alternatingly arranged.

When the first magnetic layer 11 includes Co, the portion of the first magnetic layer 11 on a side of the first nonmagnetic layer 11*n* preferably includes Co. When the first counter magnetic layer 11*o* includes Co, the portion of the first counter magnetic layer 11*o* on a side of the first nonmagnetic layer 11*n* preferably includes Co.

As shown in FIG. 4A, the first extending portion 11*x* includes the first magnetic layer 11 including Co, the first counter magnetic layer 11*o* including Co, the first nonmagnetic layer 11*n* provided between the first magnetic layer 11 and the first counter magnetic layer 11*o* and including Cu. The first magnetic layer 11 includes a first magnetic region r1 and a second magnetic region r2. The first magnetic region r1 is between the first nonmagnetic layer 11*n* and the second magnetic region r2. A concentration of Co in the first magnetic region r1 is higher than a concentration of Co in the second magnetic region r2. The first counter magnetic layer 11*o* includes a first counter magnetic region ro1 and a second counter magnetic region ro2. The first counter magnetic region ro1 is between the first nonmagnetic layer 11*n* and the second counter magnetic region ro2. A concentration of Co in the first counter magnetic region ro1 is higher than a concentration of Co in the second counter magnetic region ro2. With such a configuration, a high MR ratio can be obtained. For example, the rate of change in the resistance of the first intermediate portion pM1 becomes high.

FIGS. 5A to 5D are schematic views illustrating a part of the magnetic sensor according to the first embodiment.

Figure 5A:
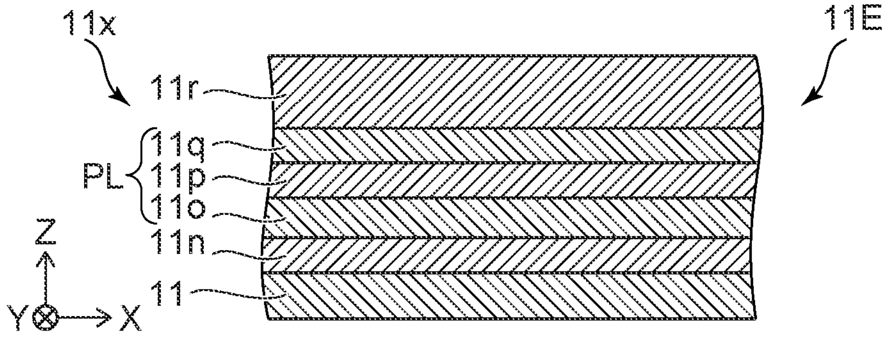
FIGS. 5A to 5D are schematic views illustrating a part of the magnetic sensor according to the first embodiment.
Figure 5B:
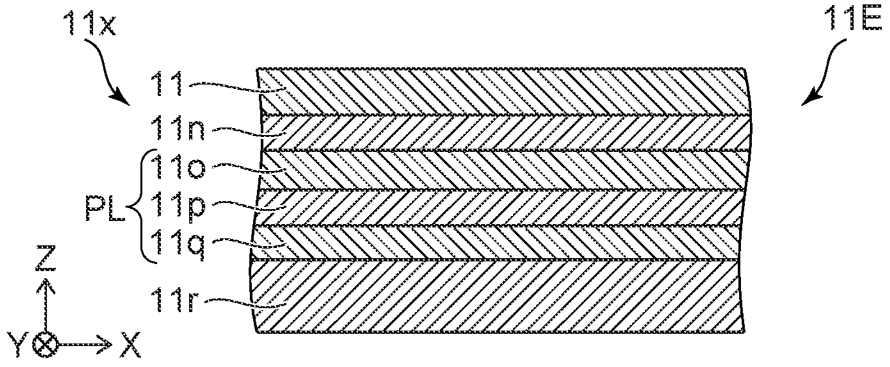
Figure 5C:
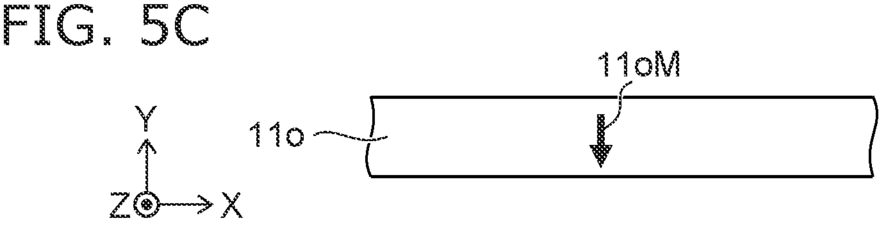
Figure 5D:
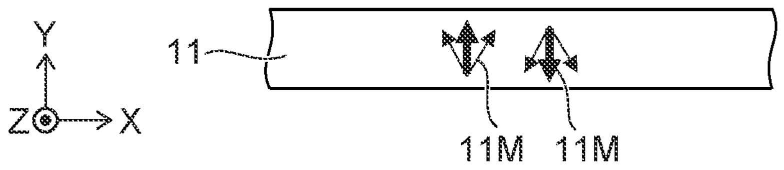

FIGS. 5A and 5B are cross-sectional views. FIG. 5C is a plan view of the first counter magnetic layer 11*o*. FIG. 5D is a plan view of the first magnetic layer 11.

As shown in FIG. 5A, in this example, the first extending portion 11*x* includes the first magnetic layer 11, the first layer 11*r*, the first counter magnetic layer 11*o*, and the first nonmagnetic layer 11*n*. The first layer 11*r* includes, for example, at least one selected from the group consisting of IrMn and PtMn. The first layer 11*r* is, for example, an antiferromagnetic layer. The first counter magnetic layer 11*o* is provided between the first magnetic layer 11 and the first layer 11*r*. The first nonmagnetic layer 11*n* is provided between the first magnetic layer 11 and the first counter magnetic layer 11*o*.

In this example, the first extending portion 11*x* further includes a first magnetic film 11*q* and a first nonmagnetic film 11*p*. The first magnetic film 11*q* is provided between the first counter magnetic layer 11*o* and the first layer 11*r*. The first nonmagnetic film 11*p* is provided between the first counter magnetic layer 11*o* and the first magnetic film 11*q*. The first magnetic film 11*q* may have a function of increasing the magnetization pinning force of the first counter magnetic layer 11*o* in combination with the first nonmagnetic film 11*p*.

In this example, the first magnetic layer 11, the first counter magnetic layer 11*o*, and the first magnetic film 11*q* include at least one selected from the group consisting of Fe, Co, and Ni. The first nonmagnetic layer 11*n* includes, for example, Cu. The first nonmagnetic film 11*p* includes Ru.

As shown in FIG. 5B, the stacking order (upper and lower) of the magnetic layers may be reversed from the example of FIG. 5A.

In the examples of FIGS. 5A and 5B, the first counter magnetic layer 11*o* (or the combination of the first counter magnetic layer 11*o*, the first nonmagnetic film 11*p*, and the first magnetic film 11*q*) functions as magnetization reference layer. For example, as shown in FIG. 5C, the magnetization 11*o*M of the first counter magnetic layer 11*o* substantially follows the third direction (Y-axis direction) in a state where a magnetic field is not substantially applied. Even when a magnetic field is applied, the magnetization 11*o*M substantially follows the third direction (Y-axis direction).

For example, as shown in FIG. 5D, the magnetization 11M of the first magnetic layer 11 substantially follows the third direction (Y-axis direction) in a state where a magnetic field is not substantially applied. When a magnetic field including a component in the second direction (X-axis direction) is applied, the direction of the magnetization 11M changes according to the magnetic field. The first magnetic layer 11 is, for example, a magnetization free layer. In a state where a magnetic field is not substantially applied, the direction of the magnetization 11M of the first magnetic layer 11 may be "parallel" or "antiparallel" with respect to the magnetization 11*o*M of the first counter magnetic layer 11*o*.

For example, in the examples shown in FIGS. 4A to 4C and 5A to 5D, the electrical resistance of the first magnetic element 11E (or the first extending portion 11*x*) is substantially an even function with respect to the magnetic field applied from the outside. An example of the characteristics of even functions will be described later.

Figure 6A:
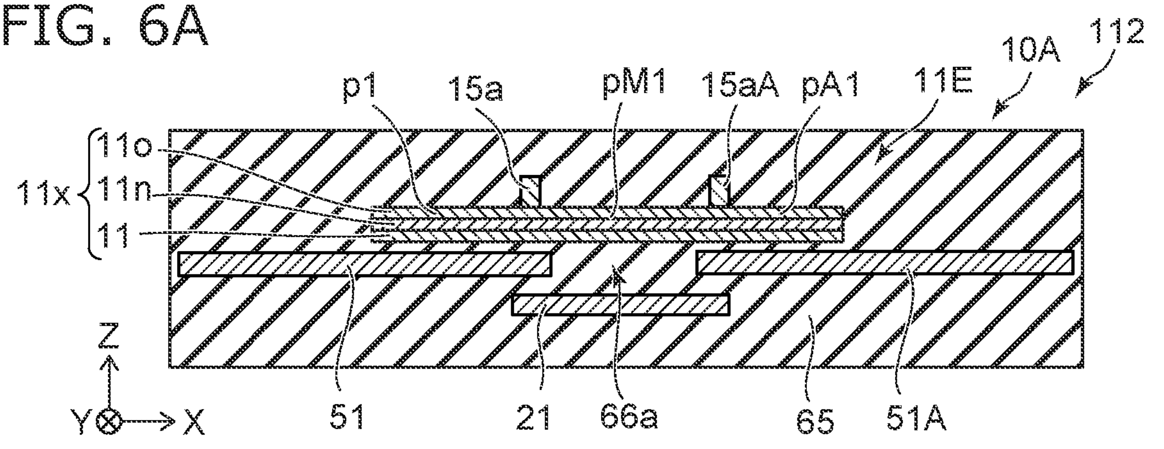
FIGS. 6A and 6B are schematic views illustrating a magnetic sensor according to the first embodiment.
Figure 6B:
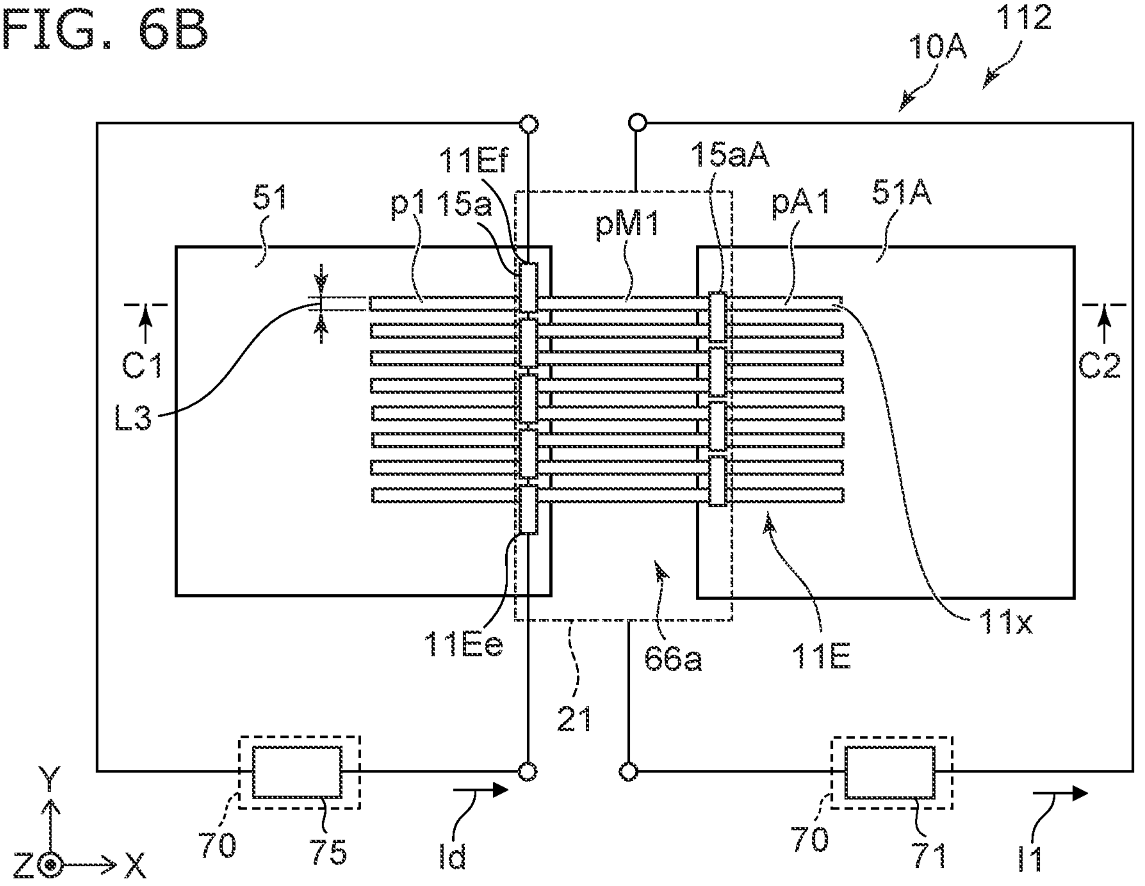

FIGS. 6A and 6B are schematic views illustrating a magnetic sensor according to the first embodiment.

FIG. 6A is a cross-sectional view taken along C1-C2 line of FIG. 6B. FIG. 6 is a plan view.

As shown in FIGS. 6A and 6B, in a magnetic sensor 112 according to the embodiment, the first sensor part 10A further includes the first conductive member 21 in addition to the first magnetic member 51, the first counter magnetic member 51A, and the first magnetic element 11E. Except for the first conductive member 21, the configuration of the magnetic sensor 112 may be the same as the configuration of the magnetic sensor 110 or the magnetic sensor 111. In this example, the first magnetic element 11E includes a plurality of first extending portions 11*x*.

As shown in FIG. 6A, at least a part of the first conductive member 21 overlaps the region 66*a* between the first magnetic member 51 and the first counter magnetic member 51A in the second direction (Z-axis direction). As shown in FIG. 6B, a first current I1 including an AC component is possible to flow through the first conductive member 21. The first current I1 is along the third direction (Y-axis direction).

The magnetic sensor 112 may further include a first current circuit 71. The first current circuit 71 can supply the first current I1 to the first conductive member 21.

A magnetic field (current magnetic field) due to the first current I1 supplied to the first conductive member 21 is applied to the first magnetic element 11E. This current magnetic field is collected by the first magnetic member 51 and the first counter magnetic member 51A, and is efficiently applied to the first extending portion 11*x*.

By applying an alternating magnetic field based on the first current I1 including alternating current to the first magnetic element 11E having the characteristic of an even function, detection with higher sensitivity becomes possible as described later.

Hereinafter, an example of a change in the electrical resistance of the first magnetic element 11E when a current flows through the first conductive member 21 will be described.

Figure 7A:
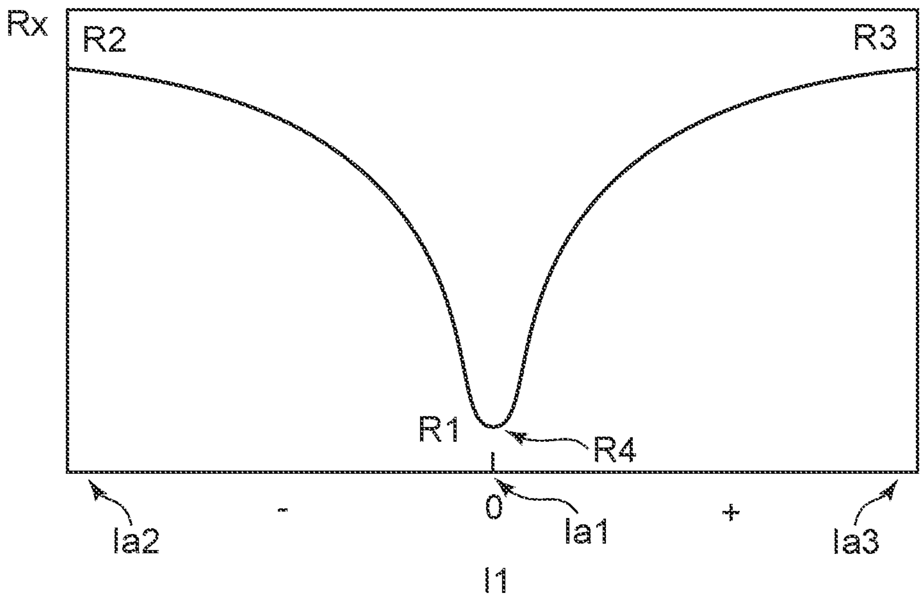
FIGS. 7A and 7B are graphs illustrating characteristics of the magnetic sensor according to the first embodiment.
Figure 7B:
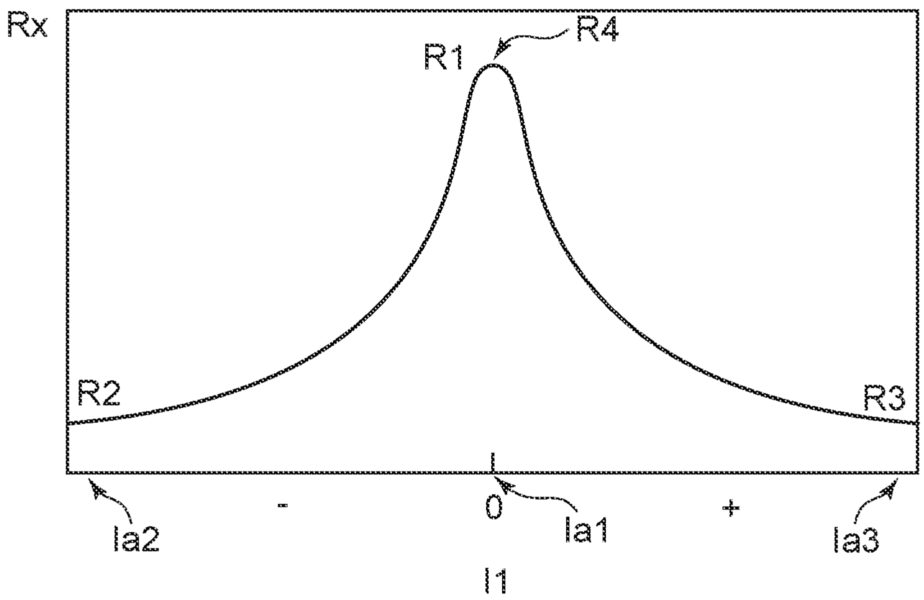

FIGS. 7A and 7B are schematic views illustrating the characteristics of the magnetic sensor according to the first embodiment.

The horizontal axis of these figures corresponds to the value of the current (for example, the first current I1) flowing through the first conductive member 21. The vertical axis is the electric resistance Rx of the first magnetic element 11E (for example, the first extending portion 11*x*). As shown in FIGS. 7A and 7B, in the embodiment, the electric resistance Rx shows the characteristic of an even function with respect to the change of the current (first current I1).

For example, the electric resistance Rx of the first magnetic element 11E has a first value R1 when a first value current Ia1 is supplied to the first conductive member 21. The electric resistance Rx has a second value R2 when a second value current Ia2 is supplied to the first conductive member 21. The electric resistance Rx has a third value R3 when a third value current Ia3 is supplied to the first conductive member 21. The absolute value of the first value current Ia1 is smaller than the absolute value of the second value current Ia2 and smaller than the absolute value of the third value current Ia3. The first value current Ia1 may be, for example, substantially 0. The direction of the second value current Ia2 is opposite to the direction of the third value current Ia3.

In the example of FIG. 7A, the first value R1 is lower than the second value R2 and lower than the third value R3. In the example of FIG. 7A, the electrical resistance Rx has a "valley-shaped" characteristic. The first value R1 is, for example, the lowest value of electrical resistance. In the example of FIG. 7B, the first value R1 is higher than the second value R2 and higher than the third value R3. In the example of FIG. 7B, the electrical resistance Rx has a "mountain-shaped" characteristic. The first value R1 is, for example, the maximum value of electrical resistance.

For example, when the external magnetic field is substantially 0, the magnetization of the first magnetic layer 11 and the magnetization of the first counter magnetic layer 11*o* are in a "parallel array", and for example, when interlayer magnetic coupling acts, "valley-shaped" characteristics are obtained. At this time, for example, the thickness of the first nonmagnetic layer 11*n* is not less than 2.5 nm. For example, when the external magnetic field is substantially 0, the magnetization of the first magnetic layer 11 and the magnetization of the first opposed magnetic layer 11*o* are in an "antiparallel array", and for example, when interlayer magnetic coupling acts, the characteristics of "mountain shape" are obtained. In this case, the thickness of the first nonmagnetic layer 11*n* is, for example, not less than 1.9 nm and not more than 2.1 nm.

For example, when no current flows through the first conductive member 21, the electric resistance Rx has a fourth value R4. For example, the first value R1 is substantially the same as the fourth value R4 when no current flows. For example, the ratio of the absolute value of the difference between the first value R1 and the fourth value R4 to the fourth value R4 is not more than 0.01. The ratio may be not more than 0.001. For positive and negative currents, the characteristics of an even function are obtained.

The relationship between the first current I1 and the electric resistance Rx is based on that the magnetic field due to the first current I1 is applied to the first magnetic element 11E, and the electric resistance Rx of the first magnetic element 11E changes depending on the strength of the magnetic field.

The electric resistance Rx when an external magnetic field is applied to the first magnetic element 11E also shows the characteristics of an even function as in the example shown in FIG. 7A or FIG. 7B. The external magnetic field includes, for example, components along the X-axis direction.

Figure 8A:
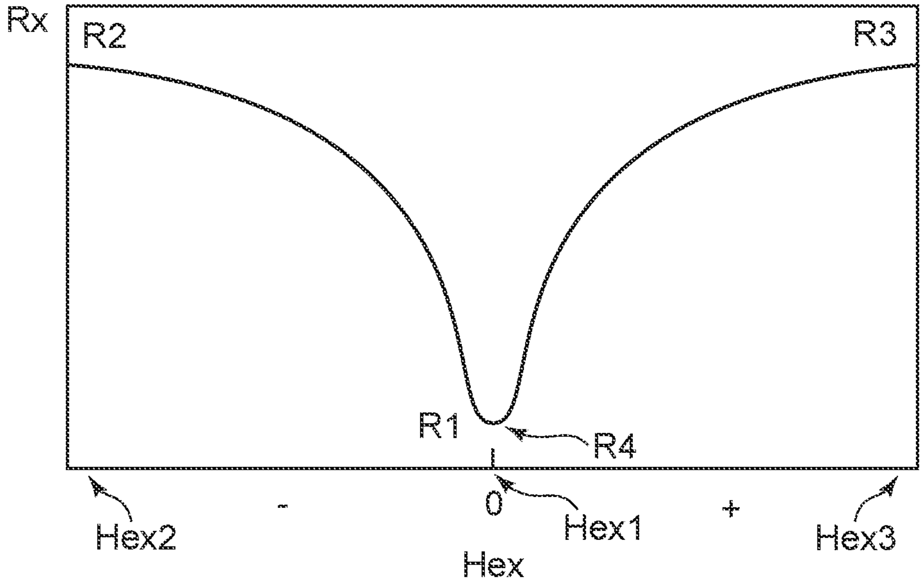
FIGS. 8A and 8B are graphs illustrating characteristics of the magnetic sensor according to the first embodiment.
Figure 8B:
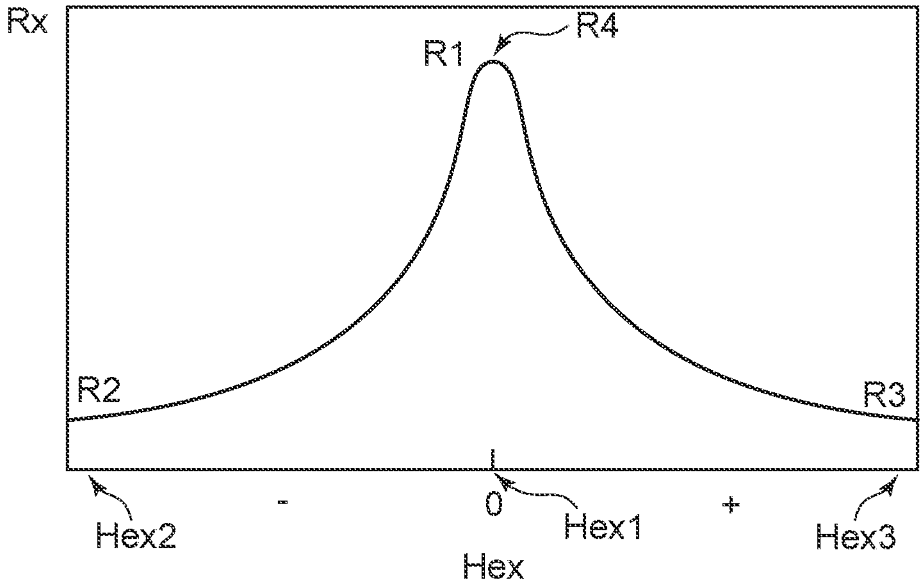

FIGS. 8A and 8B are schematic views illustrating the characteristics of the magnetic sensor according to the first embodiment.

The horizontal axis in these figures is the intensity of the external magnetic field Hex applied to the first magnetic element 11E. The vertical axis is the electric resistance Rx of the first magnetic element 11E. These figures correspond to the R-H characteristics. As shown in FIGS. 8A and 8B, the electric resistance Rx has characteristics of an even function with respect to the magnetic field (external magnetic field Hex, for example, the magnetic field in the X-axis direction) applied to the first magnetic element 11E.

As shown in FIGS. 8A and 8B, the electric resistance Rx of the first magnetic element 11E has the first value R1 when a first magnetic field Hex1 is applied to the first magnetic element 11E. The electric resistance Rx has the second value R2 when a second magnetic field Hex2 is applied to the first magnetic element 11E. The electric resistance Rx has the third value R3 when a third magnetic field Hex3 is applied to the first magnetic element 11E. The absolute value of the first magnetic field Hex1 is smaller than the absolute value of the second magnetic field Hex2 and smaller than the absolute value of the third magnetic field Hex3. The direction of the second magnetic field Hex2 is opposite to the direction of the third magnetic field Hex3.

In the example of FIG. 8A, the first value R1 is lower than the second value R2 and lower than the third value R3. In the example of FIG. 8B, the first value R1 is higher than the second value R2 and higher than the third value R3. For example, when no external magnetic field is applied to the first magnetic element 11E, the electric resistance Rx has a fourth value R4. The first value R1 is substantially the same as the fourth value R4 when no external magnetic field is applied. For example, the ratio of the absolute value of the difference between the first value R1 and the fourth value R4 to the fourth value R4 is not more than 0.01. The ratio may be not more than 0.001. The characteristics of even functions are obtained with respect to positive and negative external magnetic fields.

Utilizing such characteristics of even functions, high-sensitivity detection is possible as follows.

In the following, an example will be described in which the first current I1 is an alternating current and does not substantially include a direct current component. A first current I1 (alternating current) is supplied to the first conductive member 21, and an alternating magnetic field generated by the alternating current is applied to the first magnetic element 11E. An example of the change in the electric resistance Rx at this time will be described.

Figure 9A:
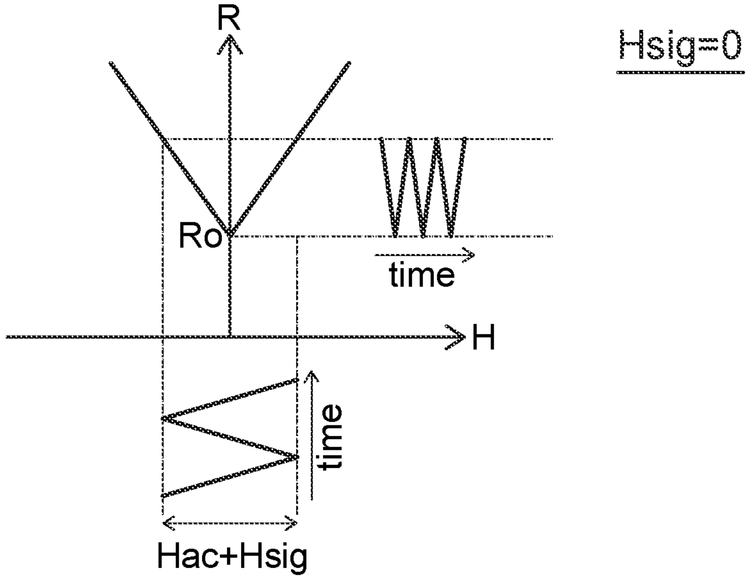
FIGS. 9A to 9C are graphs illustrating characteristics of the magnetic sensor according to the first embodiment.
Figure 9B:
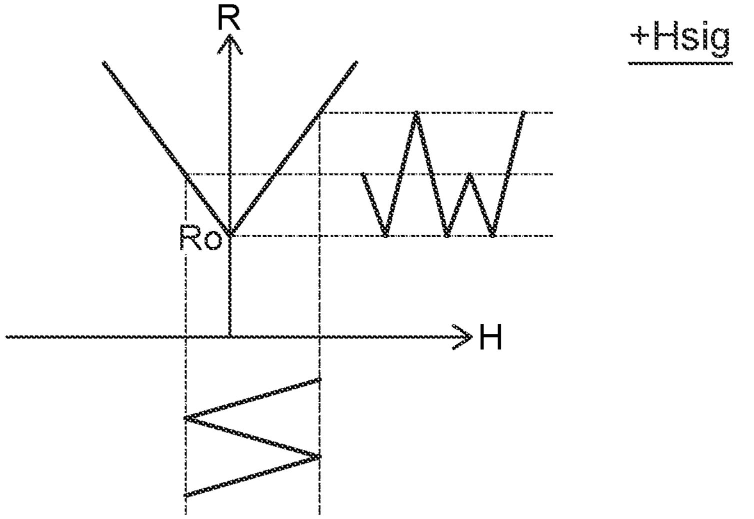
Figure 9C:
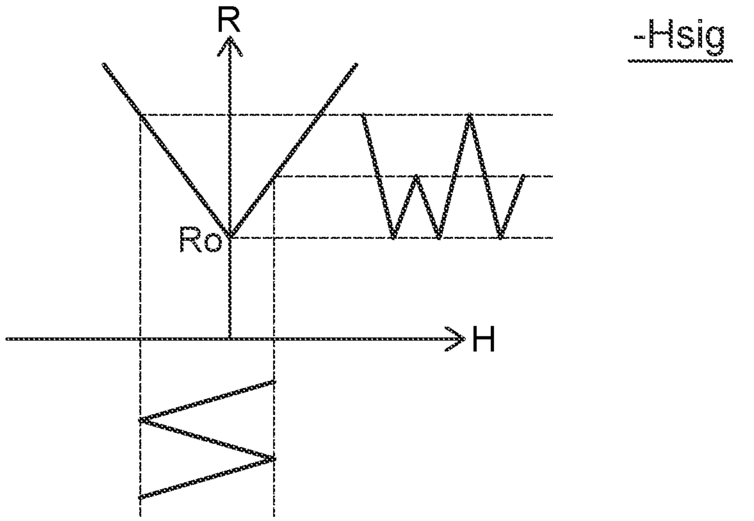

FIGS. 9A to 9C are graphs illustrating characteristics of the magnetic sensor according to the first embodiment.

FIG. 9A shows the characteristics when a signal magnetic field Hsig (external magnetic field) applied to the first magnetic element 11E is 0. FIG. 9B shows the characteristics when the signal magnetic field Hsig is positive. FIG. 9C shows the characteristics when the signal magnetic field Hsig is negative. These figures show the relationship between the magnetic field H and the resistance R (corresponding to the electric resistance Rx).

As shown in FIG. 9A, when the signal magnetic field Hsig is 0, the resistor R exhibits a characteristic symmetric with respect to the positive and negative magnetic fields H. When an alternating current magnetic field Hac is zero, the resistance R is a low resistance Ro. For example, the magnetization of the magnetization free layer rotates in substantially the same manner with respect to the positive and negative magnetic fields H. Therefore, a symmetrical change in resistance is obtained. The fluctuation of the resistance R with respect to the alternating current magnetic field Hac has the same value with positive and negative polarities. The period of change of the resistance R is ½ times the period of the alternating current magnetic field Hac. The change in resistance R has substantially no frequency component of the alternating current magnetic field Hac.

As shown in FIG. 9B, when a positive signal magnetic field Hsig is applied, the characteristic of the resistor R shifts to the side of the positive magnetic field H. In the alternating current magnetic field Hac on the positive side, for example, the resistance R becomes high. In the alternating current magnetic field Hac on the negative side, the resistance R becomes low.

As shown in FIG. 9C, when a negative signal magnetic field Hsig is applied, the characteristic of the resistor R shifts to the side of the negative magnetic field H. In the alternating current magnetic field Hac on the positive side, for example, the resistance R becomes low. In the alternating current magnetic field Hac on the negative side, the resistance R becomes high.

When a signal magnetic field Hsig of a predetermined magnitude is applied, the resistance R fluctuates differently with respect to the positive and negative of the alternating current magnetic field Hac. The period of fluctuation of the resistance R with respect to the positive and negative of the alternating current magnetic field Hac is the same as the period of the alternating current magnetic field Hac. The output voltage of the AC frequency component corresponding to the signal magnetic field Hsig is generated.

The above characteristics are obtained when the signal magnetic field Hsig does not change with time. When the signal magnetic field Hsig changes with time, it becomes as follows. The frequency of the signal magnetic field Hsig is defined as the signal frequency fsig. The frequency of the alternating current magnetic field Hac is defined as the AC frequency fac. At this time, an output corresponding to the signal magnetic field Hsig is generated at a frequency of fac±fsig.

When the signal magnetic field Hsig changes with time, the signal frequency fsig is, for example, not more than 1 kHz. On the other hand, the AC frequency fac is sufficiently higher than the signal frequency fsig. For example, the AC frequency fac is not less than 10 times the signal frequency fsig.

For example, the signal magnetic field Hsig can be detected with high accuracy by extracting the output voltage of a component (AC frequency component) having the same period (frequency) as the period (frequency) of the alternating current magnetic field Hac. In the magnetic sensor 112 according to the embodiment, the external magnetic field Hex (signal magnetic field Hsig) to be detected can be detected with high sensitivity by utilizing such characteristics. In the embodiment, the external magnetic field Hex (signal magnetic field Hsig) and the alternating current magnetic field Hac due to the first current I1 can be efficiently applied to the first magnetic element 11E by the first magnetic member 51 and the first counter magnetic member 51A. High sensitivity is obtained.

Figure 10A:
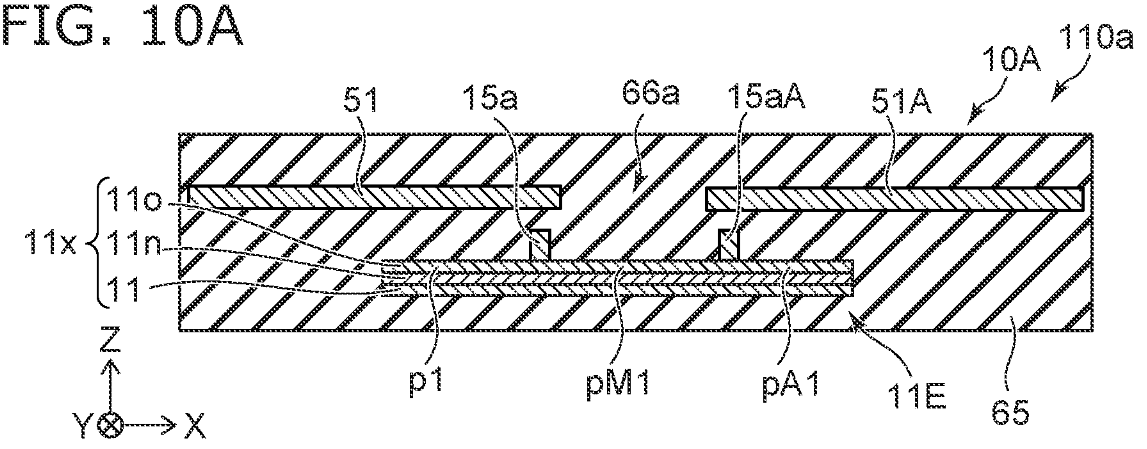
FIGS. 10A to 10C are schematic cross-sectional views illustrating magnetic sensors according to the first embodiment.
Figure 10B:
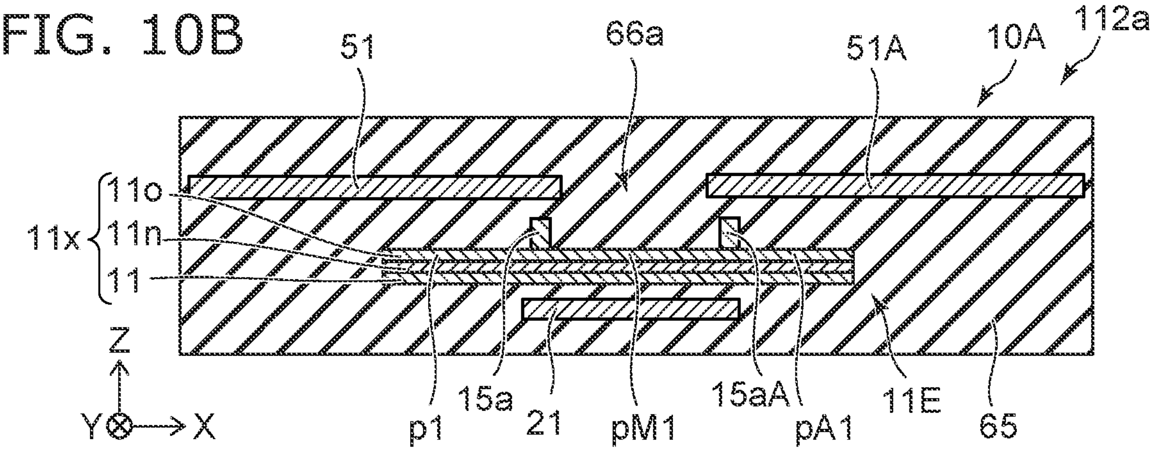
Figure 10C:
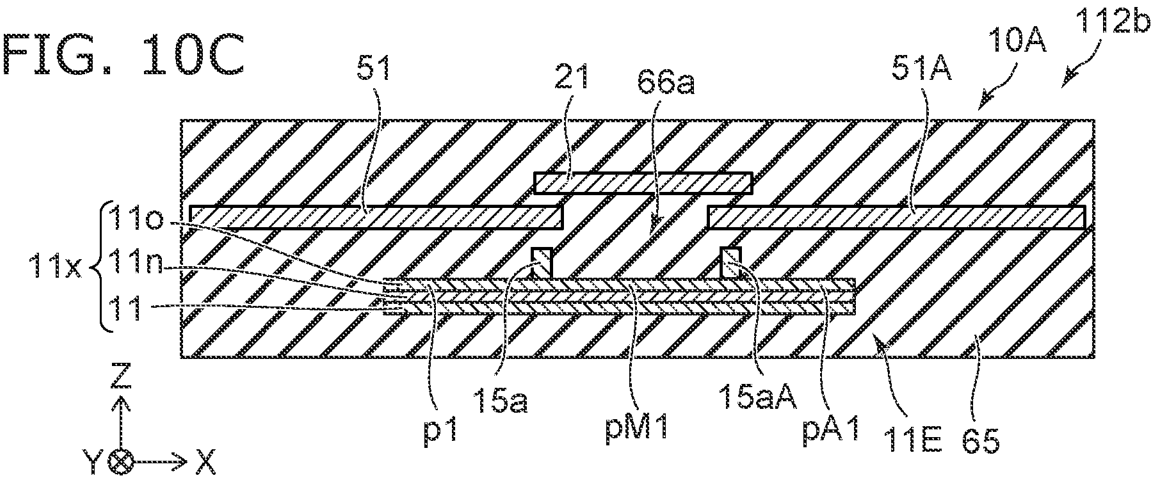

FIGS. 10A to 10C are schematic cross-sectional views illustrating magnetic sensors according to the first embodiment.

As shown in FIG. 10A, in a magnetic sensor **110*a* according to the embodiment, the first electrode 15*a* is between the first portion p1 and the first magnetic member 51 in the Z-axis direction. The first counter electrode 15*a*A is between the first facing portion pA1 and the first counter magnetic member 51A in the Z-axis direction. Other configurations of the magnetic sensor 110*a* may be the same as those of the magnetic sensor 110**.

As shown in FIG. 10B, in a magnetic sensor **112*a* according to the embodiment, the first extending portion 11*x* is between the first conductive member 21 and the first magnetic member 51 and between the first conductive member 21 and the first counter magnetic member 51A in the Z-axis direction. The first electrode 15*a* is between the first portion p1 and the first magnetic member 51 in the Z-axis direction. The first counter electrode 15*a*A is between the first counter portion pA1 and the first counter magnetic member 51A in the Z-axis direction. Other configurations of the magnetic sensor 112*a* may be the same as those of the magnetic sensor 112**.

As shown in FIG. 10C, in a magnetic sensor **112*b* according to the embodiment, the first magnetic member 51 and the first counter magnetic member 51A are between the first extending portion 11*x* and the first conductive member 21 in the Z-axis direction. Other configurations of the magnetic sensor 112*b* may be the same as those of the magnetic sensor 112**.

High sensitivity is also obtained in the magnetic sensors **110*a*, 112*a* and 112*b*. Noise can be reduced. The above configurations of the magnetic sensors 110*a*, 112*a* and 112*b*** may be applied to any of the embodiments described below.

Figure 11A:
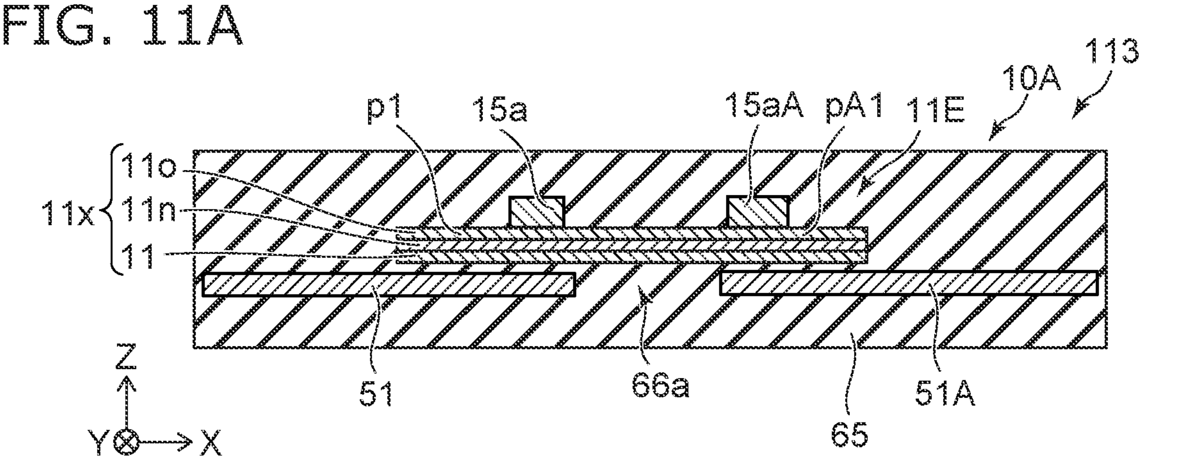
FIGS. 11A and 11B are schematic views illustrating a magnetic sensor according to the first embodiment.
Figure 11B:
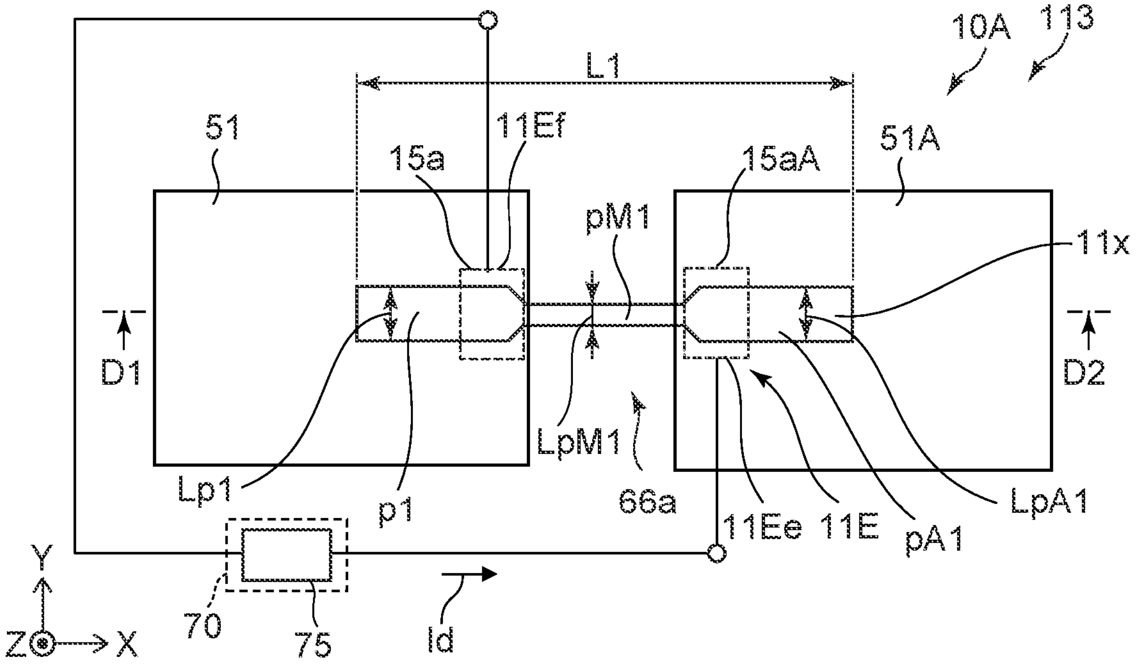

FIGS. 11A and 11B are schematic views illustrating a magnetic sensor according to the first embodiment.

FIG. 11A is a cross-sectional view taken along D1-D2 line of FIG. 11B. FIG. 11B is a plan view.

As shown in FIGS. 11A and 11B, in a magnetic sensor 113 according to the embodiment, the first sensor part 10A includes the first magnetic member 51, the first counter magnetic member 51A, and the first magnetic element 11E. In the magnetic sensor 113, the width of the first extending portion **11*x* of the first magnetic element 11E changes. Other configurations of the magnetic sensor 113 may be the same as those of the above magnetic sensors (magnetic sensors 110 to 112**).

As shown in FIGS. 11A and 11B, the first extending portion **11*x* includes the first portion p1, the first counter portion pA1, and the first intermediate portion pM1. The first intermediate portion pM1 is between the first portion p1 and the first counter portion pA1. The first intermediate portion pM1 overlaps the region 66*a* between the first magnetic member 51 and the first counter magnetic member 51**A in the second direction (Z-axis direction).

The first intermediate portion pM1 has a length LpM1 along the third direction (Y-axis direction). The first portion p1 has a length Lp1 along the third direction. The first counter portion pA1 has a length LpA1 along the third direction. These lengths are, for example, widths. The length LpM1 is shorter than the length Lp1 and shorter than the length LpA1.

For example, the first electrode 15*a* is electrically connected to the first portion p1. The first counter electrode 15*a*A is electrically connected to the first counter portion pA1. The width of the first intermediate portion pM1 for which the electric resistance is detected is narrower than the width of the first portion p1 and the first counter portion pA1. For example, the magnetic field collected by the first magnetic member 51 and the first counter magnetic member 51A is more efficiently introduced into the first extending portion 11*x* via the wide first portion p1 and the first counter portion pA1. It becomes easier to obtain higher sensitivity.

Second Embodiment

In the second embodiment, a plurality of sensor parts are provided. A plurality of sensor parts are bridged, for example. As a result, the influence of noise can be further reduced. Higher sensitivity detection is possible.

FIGS. 12, 13, and 14A to 14C are schematic views illustrating magnetic sensors according to the second embodiment.

Figure 12:
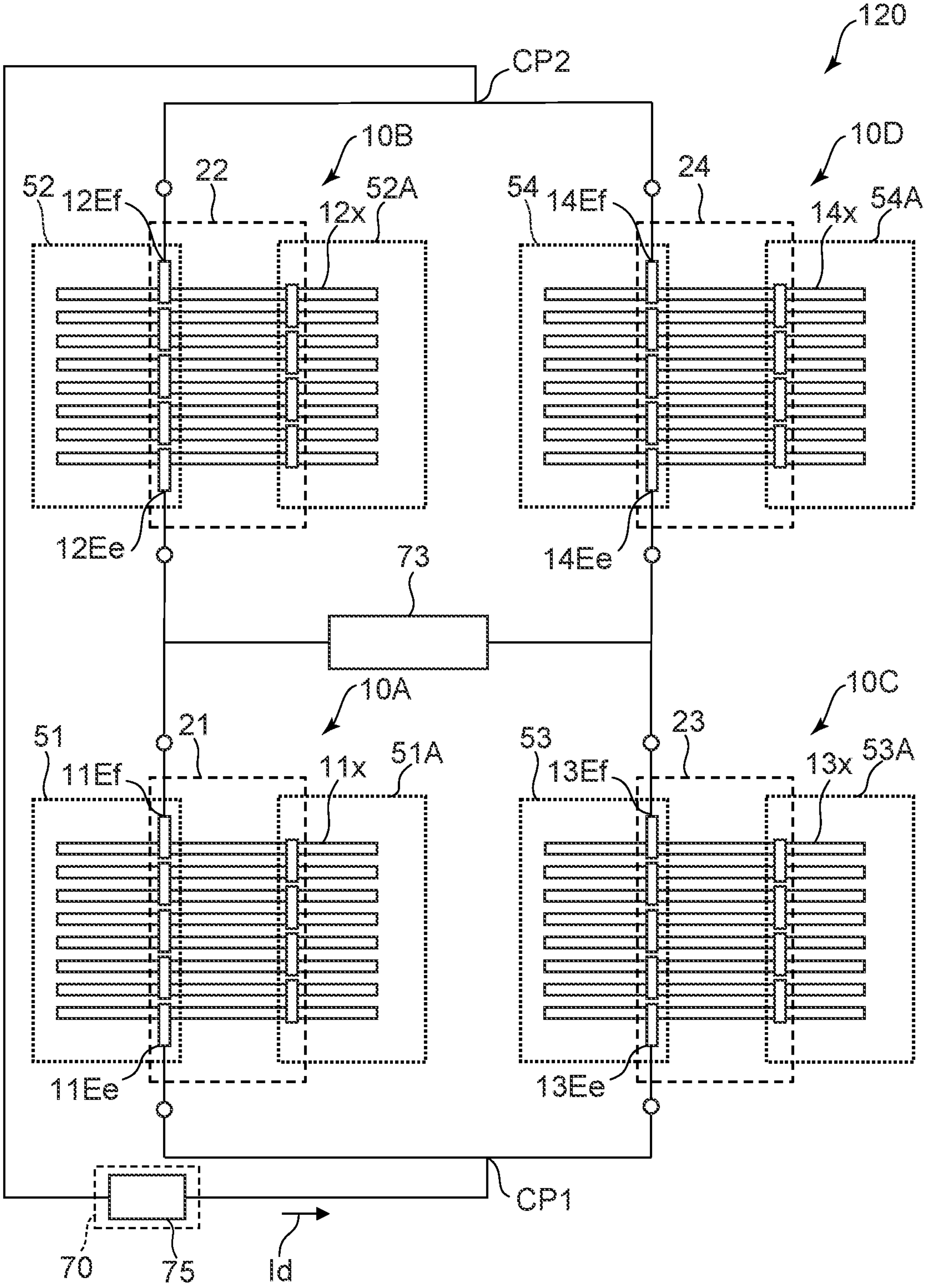
FIG. 12 is a schematic view illustrating a magnetic sensor according to a second embodiment.
Figure 13:
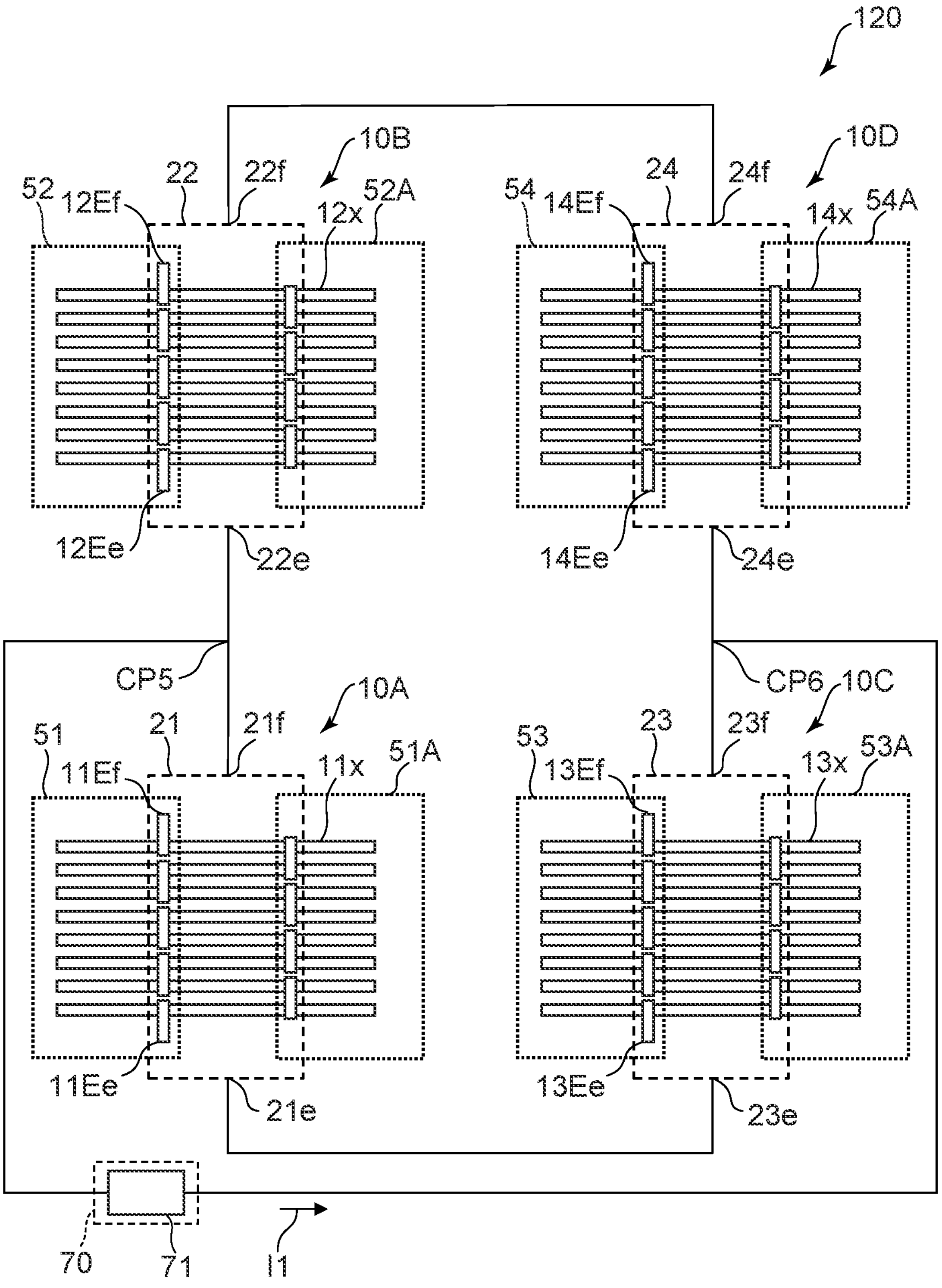
FIG. 13 is a schematic view illustrating the magnetic sensor according to the second embodiment.
Figure 14A:
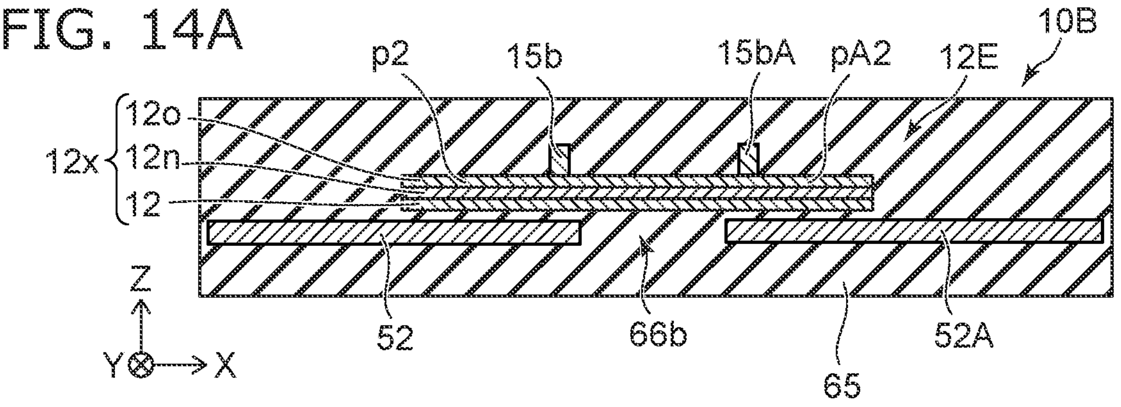
FIGS. 14A to 14C are schematic views illustrating the magnetic sensor according to the second embodiment.
Figure 14B:
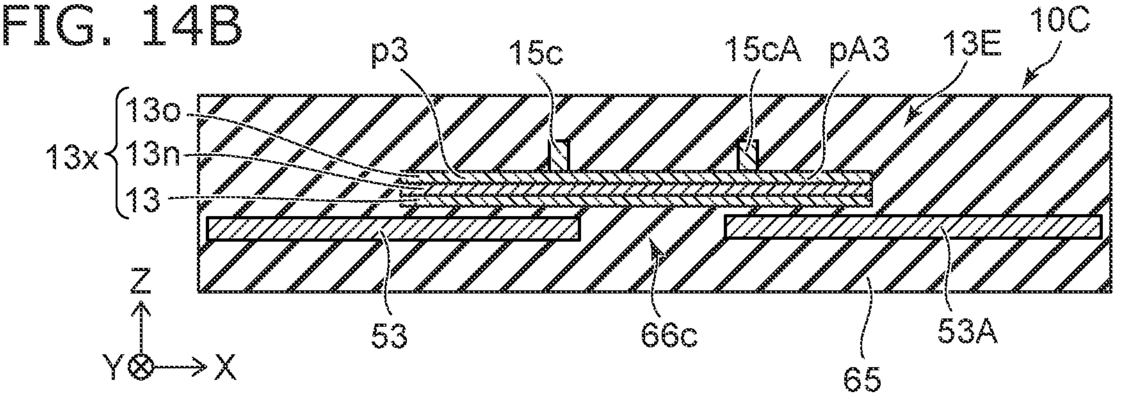
Figure 14C:
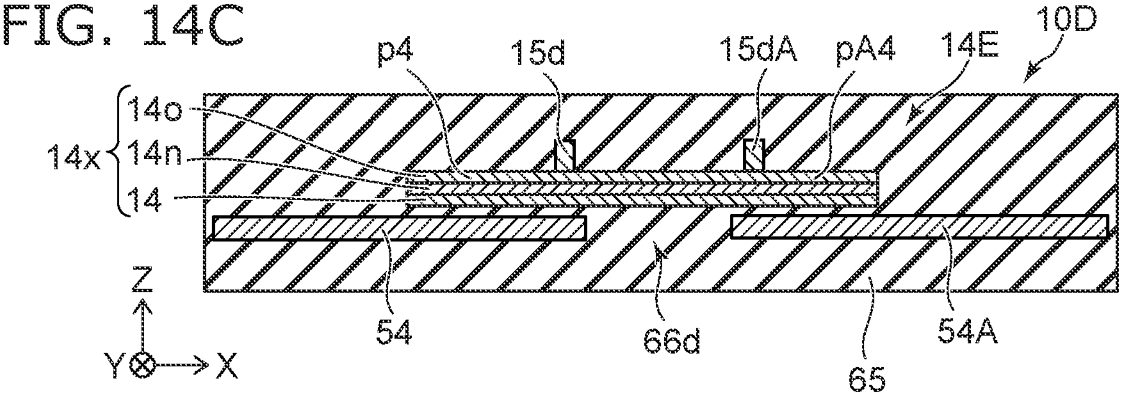

FIGS. 12 and 13 are plan views. FIGS. 14A to 14C are cross-sectional views.

As shown in FIG. 12, a magnetic sensor 120 according to the embodiment includes a second sensor part 10B, a third sensor part 10C, and a fourth sensor part 10D in addition to the first sensor part 10A described above. The magnetic sensor 120 may include the element current circuit 75, a detection circuit 73, and the first current circuit 71 (see FIG. 13). The element current circuit 75, the detection circuit 73, and the first current circuit 71 may be included in the control circuit part 70.

The second sensor part 10B includes a second magnetic element 12E. The third sensor part 10C includes a third magnetic element 13E. The fourth sensor part 10D includes a fourth magnetic element 14E. The first sensor part 10A, the second sensor part 10B, the third sensor part 10C, and the fourth sensor part 10D are electrically bridged. These magnetic elements are, for example, magneto resistance elements.

For example, one end 11Ee of the first magnetic element 11E is electrically connected to one end 13Ee of the third magnetic element 13E. The other end 11Ef of the first magnetic element 11E is electrically connected to one end 12Ee of the second magnetic element 12E. The other end 13Ef of the third magnetic element 13E is electrically connected to one end 14Ee of the fourth magnetic element 14E. The other end 12Ef of the second magnetic element 12E is electrically connected to the other end 14Ef of the fourth magnetic element 14E.

The element current circuit 75 is possible to supply the element current Id between a first connection point CP1 connecting one end 11Ee of the first magnetic element 11E to one end 13Ee of the third magnetic element 13E and a second connection point CP2 connecting the other end 12Ef of the second magnetic element 12E to the other end 14Ef of the fourth magnetic element 14E.

The detection circuit 73 is possible to detect the change in potential between a third connection point CP3 connecting the other end 11Ef of the first magnetic element 11E to one end 12Ee of the second magnetic element 12E and a fourth connection point CP4 connecting the other end 13Ef of the third magnetic element 13E to one end 14Ee of the fourth magnetic element 14E.

As shown in FIG. 13, the first sensor part 10A includes the first conductive member 21. At least a part of the first conductive member 21 overlaps the region 66*a* between the first magnetic member 51 and the first counter magnetic member 51A in the second direction (Z-axis direction) (see, for example, FIG. 6A).

As shown in FIG. 13, the second sensor part 10B includes a second magnetic member 52, a second counter magnetic member 52A, and a second conductive member 22. As shown in FIG. 14A, at least a part of the second conductive member 22 overlaps a region 66*b* between the second magnetic member 52 and the second counter magnetic member 52A in the second direction (Z-axis direction).

As shown in FIG. 13, the third sensor part 10C includes a third magnetic member 53, a third counter magnetic member 53A, and a third conductive member 23. As shown in FIG. 14B, at least a part of the third conductive member 23 overlaps a region 66*c* between the third magnetic member 53 and the third counter magnetic member 53A in the second direction (Z-axis direction).

As shown in FIG. 13, the fourth sensor part 10D includes a fourth magnetic member 54, a fourth counter magnetic member 54A, and a fourth conductive member 24. As shown in FIG. 14C, at least a part of the fourth conductive member 24 overlaps a region 66*d* between the fourth magnetic member 54 and the fourth counter magnetic member 54A in the second direction (Z-axis direction).

As shown in FIG. 13, for example, one end 21*e* of the first conductive member 21 is electrically connected to one end 23*e* of the third conductive member 23. The other end 21*f* of the first conductive member 21 is electrically connected to one end 22*e* of the second conductive member 22. The other end 23*f* of the third conductive member 23 is electrically connected to one end 24*e* of the fourth conductive member 24. The other end 22*f* of the second conductive member 22 is electrically connected to the other end 24*f* of the fourth conductive member 24.

As shown in FIG. 13, the magnetic sensor 120 may include the first current circuit 71. The first current circuit 71 is possible to supply the first current I1 including an alternating current between a fifth connection point CP5 connecting the other end 21*f* of the first conductive member 21 to one end 22*e* of the second conductive member 22, and a sixth connection point CP6 connecting the other end 23*f* of the third conductive member 23 to one end 24*e* of the fourth conductive member 24.

As described already, the first magnetic element 11E includes the first extending portion 11*x*. The first extending portion 11*x* includes the first magnetic layer 11 and the first nonmagnetic layer 11*n* provided between the first magnetic layer 11 and the first counter magnetic layer 11*o*. The first portion p1 of the first extending portion 11*x* overlaps the first magnetic member 51 in the Z-axis direction. The first counter portion pA1 of the first extending portion 11*x* overlaps the first counter magnetic member 51A in the Z-axis direction.

As shown in FIG. 14A, the second magnetic element 12E includes a second extending portion 12*x*. The second extending portion 12*x* includes a second magnetic layer 12, a second counter magnetic layer 120, and a second nonmagnetic layer 12*n* provided between the second magnetic layer 12 and the second counter magnetic layer 120. The second portion p2 of the second extending portion 12*x* overlaps the second magnetic member 52 in the Z-axis direction. The second counter portion pA2 of the second extending portion 12*x* overlaps the second counter magnetic member 52A in the Z-axis direction. For example, a second electrode 15*b* electrically connected to the second portion p2 and a second counter electrode 15*b*A electrically connected to the second counter portion pA2 are provided. For example, the second counter electrode 15*b*A may be one end 12Ee of the second magnetic element 12E. For example, the second electrode 15*b* may be the other end 12Ef of the second magnetic element 12E.

As shown in FIG. 14B, the third magnetic element 13E includes a third extending portion 13*x*. The third extending portion 13*x* includes a third magnetic layer 13 and a third counter magnetic layer 130 and a third nonmagnetic layer 13*n* provided between the third magnetic layer 13 and the third counter magnetic layer 130. The third portion p3 of the third extending portion 13*x* overlaps the third magnetic member 53 in the Z-axis direction. The third counter portion pA3 of the third extending portion 13*x* overlaps the third counter magnetic member 53A in the Z-axis direction. For example, a third electrode 15*c* electrically connected to the third portion p3 and a third counter electrode 15*c*A electrically connected to the third counter portion pA3 are provided. For example, the third counter electrode 15*c*A may be one end 13Ee of the third magnetic element 13E. For example, the third electrode 15*c* may be the other end 13Ef of the third magnetic element 13E.

As shown in FIG. 14C, the fourth magnetic element 14E includes a fourth extending portion 14*x*. The fourth extending portion 14*x* includes a fourth magnetic layer 14 and a fourth counter magnetic layer 140 and a fourth nonmagnetic layer 14*n* provided between the fourth magnetic layer 14 and the fourth counter magnetic layer 140. The fourth portion p4 of the fourth extending portion 14*x* overlaps the fourth magnetic member 54 in the Z-axis direction. The fourth counter portion pA4 of the fourth extending portion 14*x* overlaps the fourth counter magnetic member 54A in the Z-axis direction. For example, a fourth electrode 15*d* electrically connected to the fourth portion p4 and a fourth counter electrode 15*d*A electrically connected to the fourth counter portion pA4 are provided. For example, the fourth counter electrode 15*d*A may be one end 14Ee of the fourth magnetic element 14E. For example, the fourth electrode 15*d* may be the other end 14Ef of the fourth magnetic element 14E.

In the magnetic sensor 120, for example, the influence of noise can be further reduced. Higher sensitivity detection is possible.

Third Embodiment

The third embodiment relates to an inspection device. As will be described later, the inspection device may include a diagnostic device.

Figure 15:
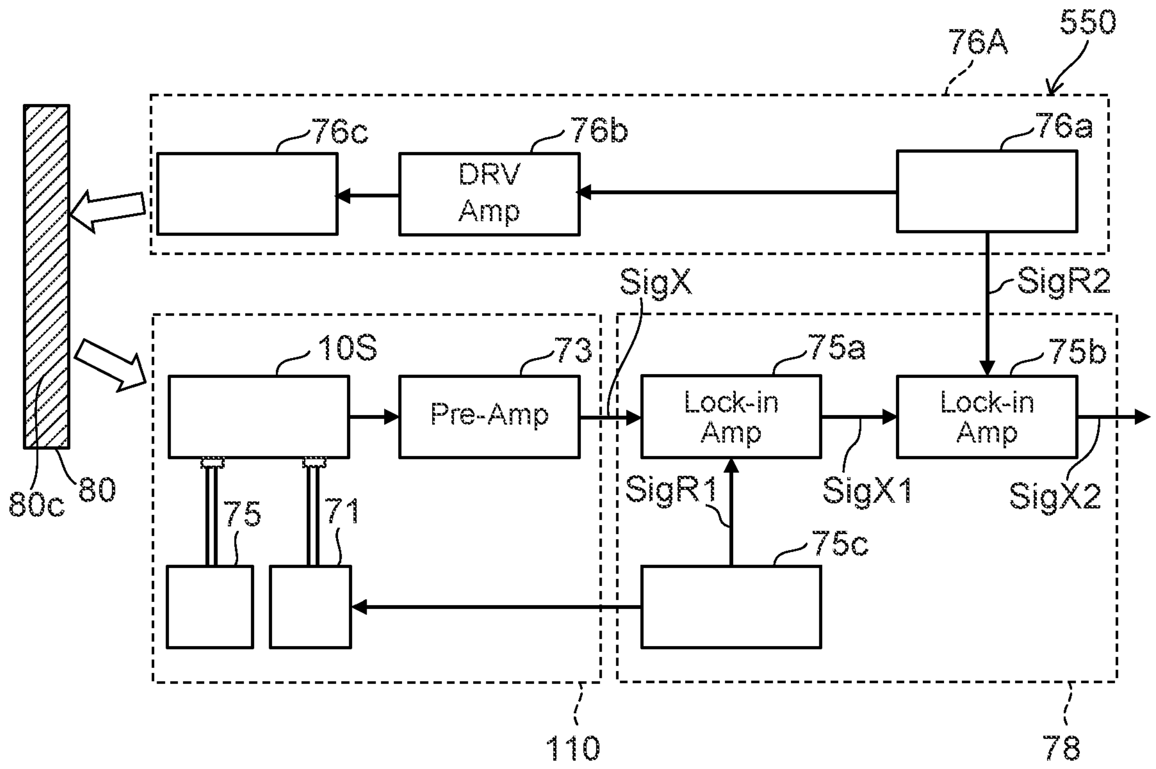
FIG. 15 is a schematic view illustrating an inspection device according to a third embodiment.

FIG. 15 is a schematic view illustrating an inspection device according to a third embodiment.

As shown in FIG. 15, an inspection device 550 according to the embodiment includes the magnetic sensor according to the embodiment (magnetic sensor 110 in the example of FIG. 15) and a processer 78. The processer 78 processes the output signal SigX obtained from the magnetic sensor 110. In this example, the processer 78 includes a sensor control circuit part 75*c*, a first lock-in amplifier 75*a*, and a second lock-in amplifier 75*b*. For example, the sensor control circuit part 75*c* controls the first current circuit 71, and the first current circuit 71 supplies the first current I1 including an AC component (see FIG. 6B and the like) to a sensor part 10S. The frequency of the AC component of the first current I1 is, for example, not more than 100 kHz. The element current Id is supplied to the sensor part 10S from the element current circuit 75. The sensor part 10S includes, for example, a first sensor part 10A and the like. The sensor part 10S may include first to fourth sensor parts 10A to 10D and the like. The detection circuit 73 detects a change in potential in the sensor part 10S. For example, the output of the detection circuit 73 becomes the output signal SigX.

In this example, the inspection device 550 includes a magnetic field application part 76A. The magnetic field application part 76A can apply a magnetic field to a detection target 80. The detection target 80 is, for example, an inspection target. The detection target 80 includes at least an inspection conductive member 80*c* such as a metal. When the magnetic field generated by the magnetic field application part 76A is applied to the inspection conductive member 80*c*, for example, an eddy current is generated in the inspection conductive member 80*c*. If the inspection conductive member 80*c* is scratched or the like, the state of the eddy current changes. By detecting the magnetic field due to the eddy current by a magnetic sensor (for example, the magnetic sensor 110), the state of the inspection conductive member 80*c* (for example, a scratch) can be inspected. The magnetic field application part 76A is, for example, an eddy current generator.

In this example, the magnetic field application part 76A includes an application control circuit part 76*a*, a drive amplifier 76*b*, and a coil 76*c*. A current is supplied to the drive amplifier 76*b* by control by the application control circuit part 76*a*. The current is, for example, alternating current. The frequency of the current is, for example, an eddy current excitation frequency. The eddy current excitation frequency is, for example, not less than 10 Hz and not more than 100 kHz. The eddy current excitation frequency may be, for example, less than 100 kHz.

For example, information on the frequency of the AC component of the first current I1 (for example, a signal) is supplied from the sensor control circuit part 75*c* to the first lock-in amplifier 75*a* as a reference wave (reference signal). The output of the first lock-in amplifier 75*a* is supplied to the second lock-in amplifier 75*b*. Information on the eddy current excitation frequency (for example, a signal) is supplied from the application control circuit part 76*a* to the second lock-in amplifier 75*b* as a reference wave (reference signal). The second lock-in amplifier 75*b* can output a signal component corresponding to the eddy current excitation frequency.

As described above, for example, the processer 78 includes the first lock-in amplifier 75*a*. The output signal SigX obtained from the magnetic sensor 110 and the signal SigR1 corresponding to the frequency of the AC component included in the first current I1 are input to the first lock-in amplifier 75*a*. The first lock-in amplifier 75*a* can output the output signal SigX1 using the signal SigR1 corresponding to the frequency of the AC component included in the first current I1 as a reference wave (reference signal). By providing the first lock-in amplifier 75*a*, noise is suppressed and high-sensitivity detection becomes possible.

The processer 78 may further include the second lock-in amplifier 75*b*. The output signal SigX1 of the first lock-in amplifier 75*a* and the signal SigR2 corresponding to the frequency (the eddy current excitation frequency) of the supply signal (in this example, the magnetic field generated by the magnetic field application part 76A) supplied toward the detection target 80 (inspection target) is input to the second lock-in amplifier 75*b*. The second lock-in amplifier

75*b* can output an output signal SigX2 using the signal SigR2 corresponding to the frequency of the supply signal supplied toward the detection target 80 (inspection target) as a reference wave (reference signal). By providing the second lock-in amplifier 75*b*, noise can be further suppressed and detection with higher sensitivity becomes possible.

The inspection device 550 can inspect abnormalities such as scratches on the inspection conductive member 80*c* of the detection target 80.

Figure 16:
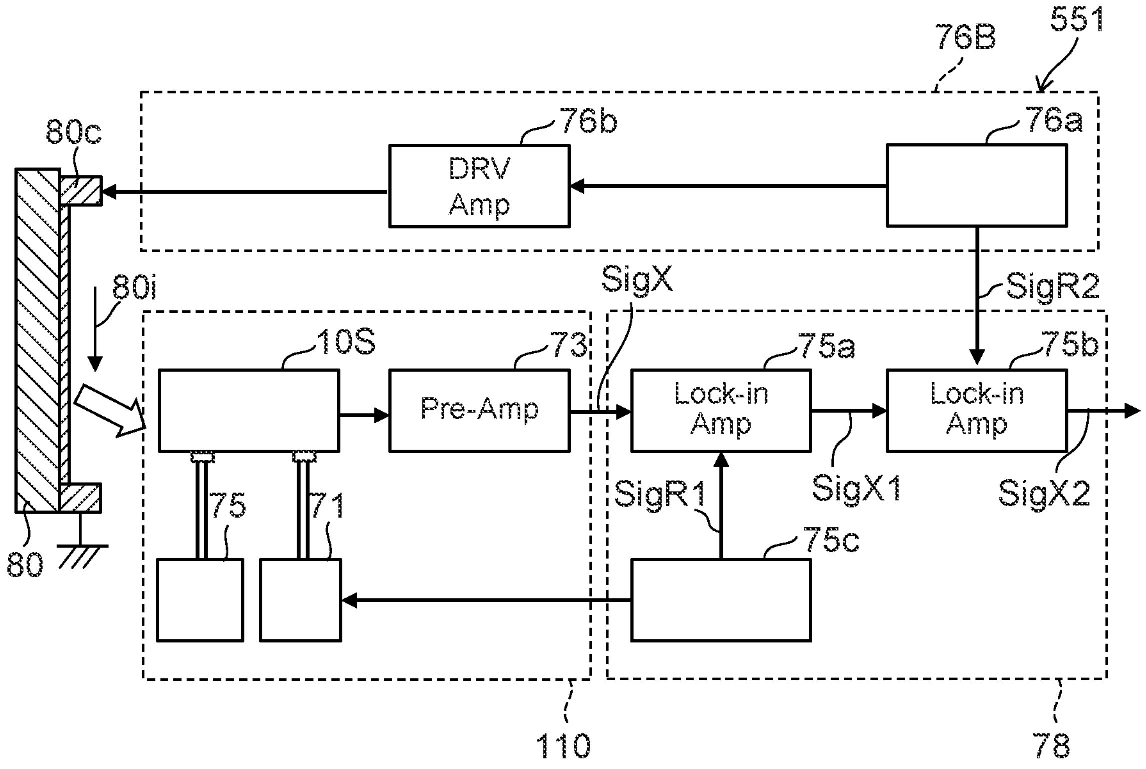
FIG. 16 is a schematic view illustrating an inspection device according to the third embodiment.

FIG. 16 is a schematic view illustrating an inspection device according to a third embodiment.

As shown in FIG. 16, an inspection device 551 according to the embodiment includes the magnetic sensor (for example, the magnetic sensor 110) according to the embodiment and the processer 78. The configuration of the magnetic sensor and the processer 78 in the inspection device 551 may be the same as those configurations in the inspection device 550. In this example, the inspection device 551 includes a detection target drive part 76B. The detection target drive part 76B can supply a current to the Inspection conductive member 80*c* included in the detection target 80. The inspection conductive member 80*c* is, for example, wirings included in the detection target 80. The magnetic field due to a current 80*i* flowing through the inspection conductive member 80*c* is detected by the magnetic sensor 110. The inspection conductive member 80*c* can be inspected based on the abnormality due to the detection result by the magnetic sensor 110. The detection target 80 may be, for example, an electronic device such as a semiconductor device. The detection target 80 may be, for example, a battery or the like.

In this example, the detection target drive part 76B includes the application control circuit part 76*a* and the drive amplifier 76*b*. The drive amplifier 76*b* is controlled by control of the application control circuit part 76*a*, and a current is supplied from the drive amplifier 76*b* to the inspection conductive member 80*c*. The current is, for example, alternating current. The frequency of the current supplies, for example, an alternating current to the inspection conductive member 80*c*. The frequency of the alternating current is, for example, not less than 10 Hz and not more than 100 kHz. The frequency may be, for example, less than 100 kHz. Also in this example, by providing the first lock-in amplifier 75*a* and the second lock-in amplifier 75*b*, for example, noise can be suppressed and high-sensitivity detection becomes possible. In one example of the inspection device 551, a plurality of magnetic sensors (for example, a plurality of magnetic sensors 110) may be provided. The plurality of magnetic sensors are, for example, sensor arrays. The sensor array allows the inspection conductive member 80*c* to be inspected in a short time. In one example of the Inspection device 551, the magnetic sensor (e.g., magnetic sensor 110) may be scanned to inspect the inspection conductive member 80*c*.

Figure 17:
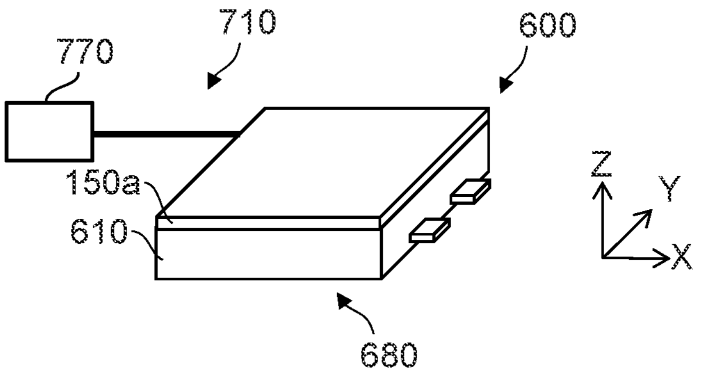
FIG. 17 is a schematic perspective view illustrating an inspection device according to the third embodiment.

FIG. 17 is a schematic perspective view illustrating an inspection device according to the third embodiment.

As shown in FIG. 17, an inspection device 710 according to the embodiment includes a magnetic sensor 150*a* and a processer 770. The magnetic sensor 150*a* may be the magnetic sensor according to any one of the first and second embodiments and a modification thereof. The processer 770 processes the output signal obtained from the magnetic sensor 150*a*. The processer 770 may compare the signal obtained from the magnetic sensor 150*a* with the reference value. The processer 770 can output the inspection result based on the processing result.

For example, the inspection device 710 inspects an inspection target 680. The inspection target 680 is, for example, an electronic device (including a semiconductor circuit or the like). The inspection target 680 may be, for example, a battery 610 or the like.

For example, the magnetic sensor 150*a* according to the embodiment may be used together with the battery 610. For example, a battery system 600 includes the battery 610 and the magnetic sensor 150*a*. The magnetic sensor 150*a* can detect the magnetic field generated by the current flowing through the battery 610.

Figure 18:
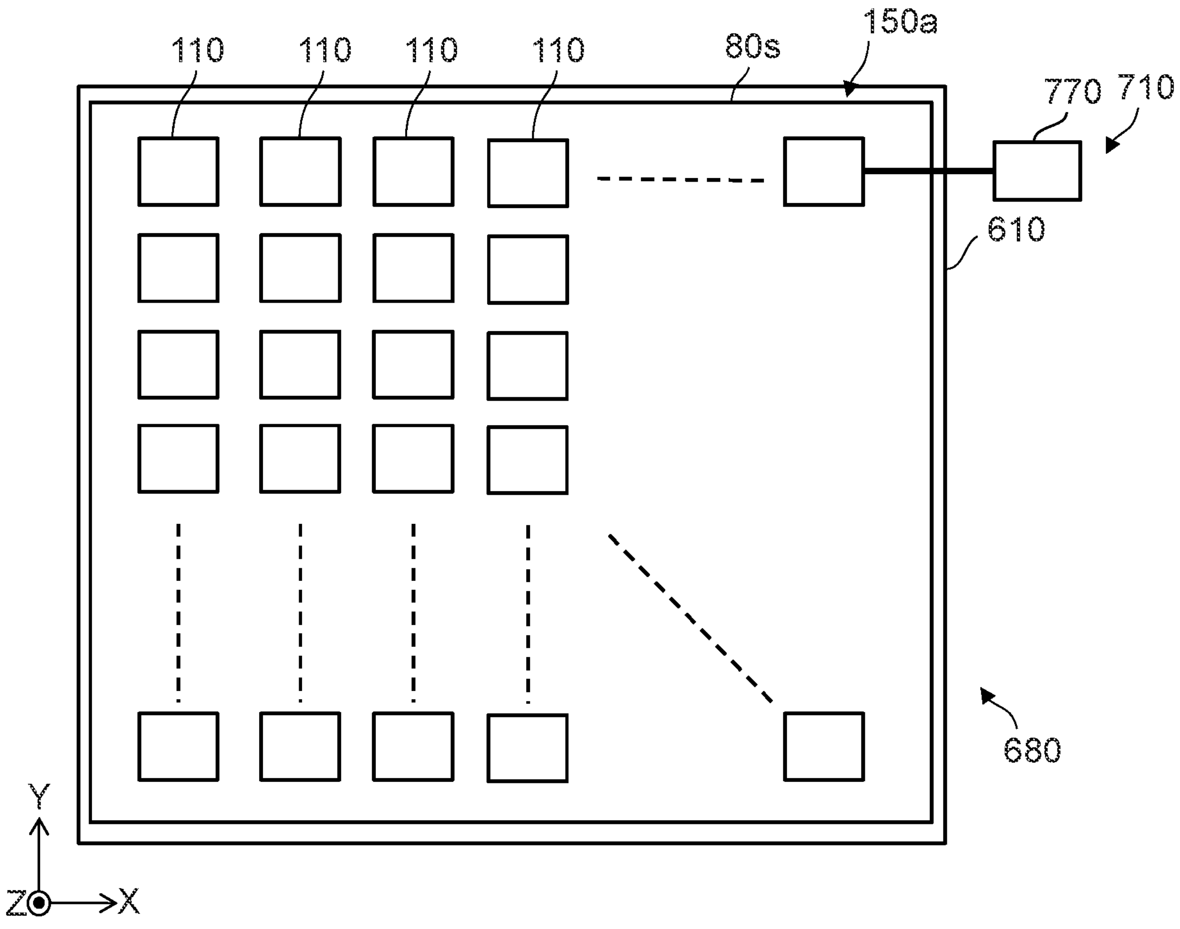
FIG. 18 is a schematic plan view illustrating an inspection device according to the third embodiment.

FIG. 18 is a schematic plan view showing the inspection device according to the third embodiment.

As shown in FIG. 18, the magnetic sensor 150*a* includes, for example, a plurality of magnetic sensors according to the embodiment. In this example, the magnetic sensor 150*a* includes a plurality of magnetic sensors (e.g., magnetic sensor 110, etc.). The plurality of magnetic sensors are arranged along, for example, two directions (for example, the X-axis direction and the Y-axis direction). The plurality of magnetic sensors 110 are provided, for example, on a substrate.

The magnetic sensor 150*a* can detect a magnetic field generated by a current flowing through the inspection target 680 (for example, a battery 610 may be used as well). For example, when the battery 610 approaches an abnormal state, an abnormal current may flow through the battery 610. By detecting an abnormal current with the magnetic sensor 150*a*, it is possible to know the change in the state of the battery 610. For example, in a state where the magnetic sensor 150*a* is placed close to the battery 610, the entire battery 610 can be inspected in a short time by using the sensor group drive means in two directions. The magnetic sensor 150*a* may be used for inspection of the battery 610 in the manufacture of the battery 610.

The magnetic sensor according to the embodiment can be applied to, for example, the inspection device 710 such as a diagnostic device.

Figure 19:
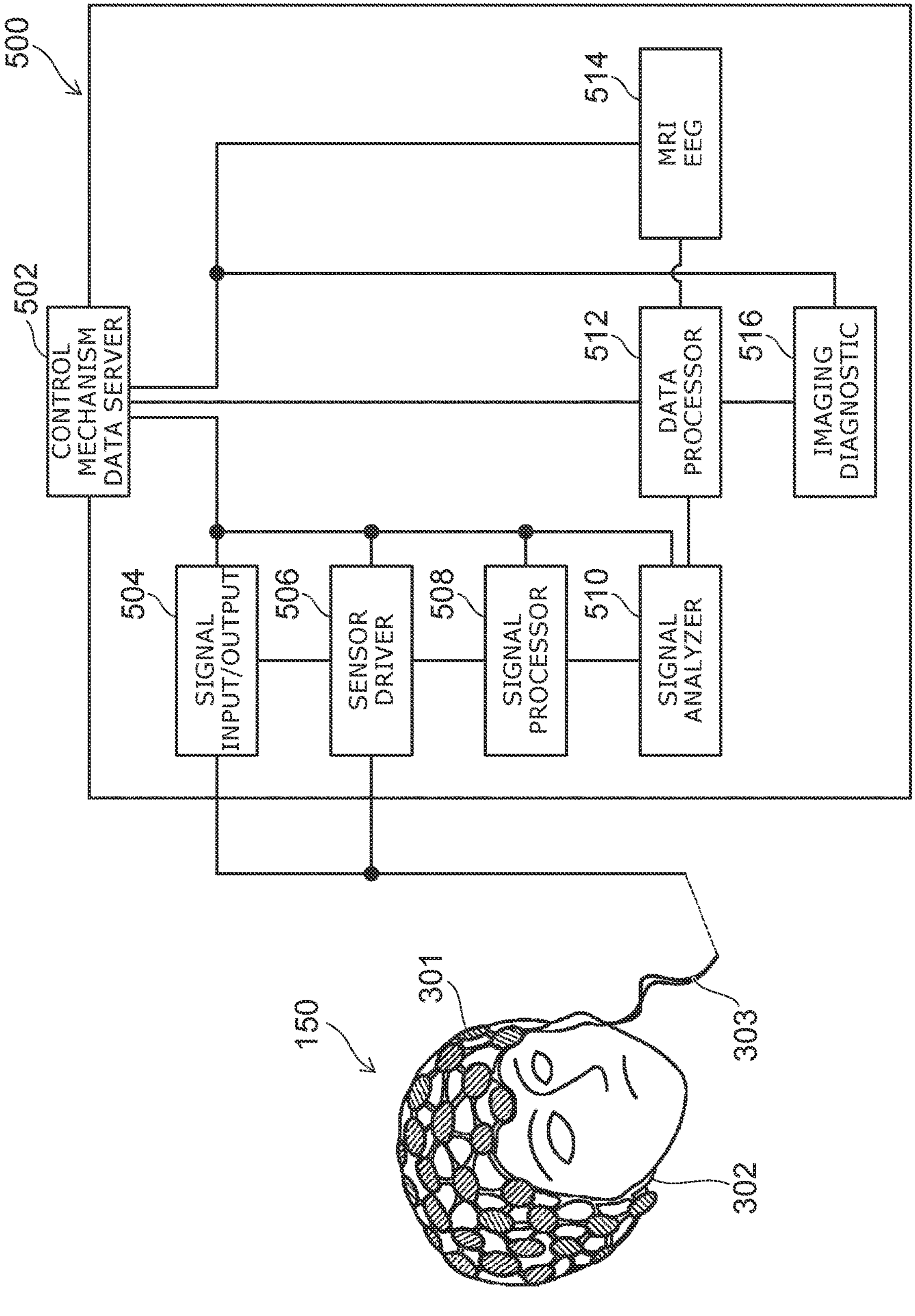
FIG. 19 is a schematic view illustrating the magnetic sensor and the inspection device according to the third embodiment.

FIG. 19 is a schematic view showing the magnetic sensor and the inspection device according to the third embodiment.

As shown in FIG. 19, a diagnosis device 500, which is an example of the inspection device 710, includes a magnetic sensor 150. The magnetic sensor 150 includes the magnetic sensors described with respect to the first and second embodiments, and modifications thereof.

In the diagnosis device 500, the magnetic sensor 150 is, for example, a magnetoencephalogram. The magnetoencephalogram detects the magnetic field generated by the cranial nerves. When the magnetic sensor 150 is used in a magnetoencephalogram, the size of the magnetic element included in the magnetic sensor 150 is, for example, not less than 1 mm and less than 10 mm. This size is, for example, the length including MFC.

As shown in FIG. 19, the magnetic sensor 150 (magnetoencephalogram) is attached to, for example, the head of a human body. The magnetic sensor 150 (magnetoencephalogram) includes a sensor part 301. The magnetic sensor 150 (magnetoencephalogram) may include a plurality of sensor parts 301. The number of the plurality of sensor parts 301 is, for example, about 100 (for example, not less than 50 and not more than 150). The plurality of sensor parts 301 are provided on a flexible base 302.

The magnetic sensor 150 may include, for example, a circuit such as differential detection. The magnetic sensor 150 may include a sensor other than the magnetic sensor (for example, a potential terminal or an acceleration sensor).

The size of the magnetic sensor 150 is smaller than the size of the conventional SQUID magnetic sensor. Therefore, it is easy to install the plurality of sensor parts 301. It is easy to install the plurality of sensor parts 301 and other circuits. The coexistence of the plurality of sensor parts 301 and other sensors is easy.

The base 302 may include an elastic body such as a silicone resin. For example, the plurality of sensor parts 301 are connected to the base 302. The base 302 can be in close contact with the head, for example.

The input/output code 303 of the sensor part 301 is connected to the sensor drive part 506 and the signal input/output part 504 of the diagnosis device 500. The magnetic field measurement is performed in the sensor part 301 based on the electric power from the sensor drive part 506 and the control signal from the signal input/output part 504. The result is input to the signal input/output part 504. The signal obtained by the signal input/output part 504 is supplied to the signal processer 508. In the signal processer 508, for example, processing such as noise removal, filtering, amplification, and signal calculation is performed. The signal processed by the signal processer 508 is supplied to the signal analyzer 510. The signal analyzer 510 extracts, for example, a specific signal for magnetoencephalography measurement. In the signal analyzer 510, for example, signal analysis for matching the signal phases is performed.

The output of the signal analyzer 510 (data for which signal analysis has been completed) is supplied to the data processer 512. The data processer 512 performs data analysis. In this data analysis, for example, image data such as MRI (Magnetic Resonance Imaging) can be incorporated. In this data analysis, for example, scalp potential information such as EEG (Electroencephalogram) can be incorporated. For example, a data part 514 such as MRI or EEG is connected to the data processer 512. By data analysis, for example, nerve ignition point analysis or inverse problem analysis is performed.

The result of the data analysis is supplied to, for example, the imaging diagnosis part 516. Imaging is performed in the imaging diagnosis part 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnosis device 500 according to the embodiment includes the magnetic sensor 150 and a processer that processes an output signal obtained from the magnetic sensor 150. This processer includes, for example, at least one of the signal processer 508 and the data processer 512. The processer includes, for example, a computer.

In the magnetic sensor 150 shown in FIG. 19, the sensor part 301 is installed on the head of the human body. The sensor part 301 may be installed on the chest of the human body. This enables magnetocardiography. For example, the sensor part 301 may be installed on the abdomen of a pregnant woman. This makes it possible to perform a fetal heartbeat test.

The magnetic sensor device including the subject is preferably installed in the shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with a shield mechanism. For example, effective shielding may be performed in signal analysis or data processing.

In embodiments, the base 302 may be flexible and may be substantially non-flexible. In the example shown in FIG. 19, the base 302 is a continuous film processed into a hat shape. The base 302 may have a net shape. Thereby, for example, good wearability can be obtained. For example, the adhesion of the base 302 to the human body is improved. The base 302 may be helmet-shaped and may be rigid.

Figure 20:
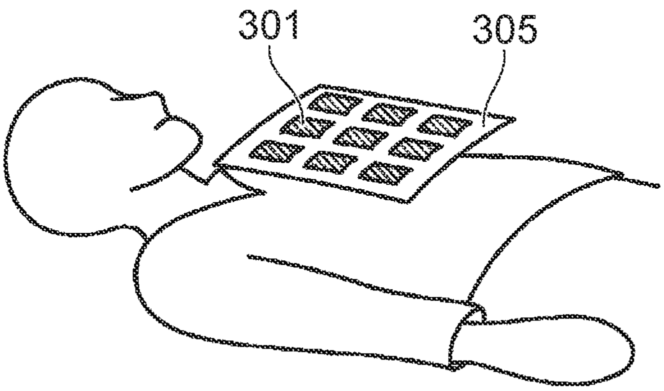
FIG. 20 is a schematic view illustrating the inspection device according to the third embodiment.

FIG. 20 is a schematic view showing the inspection device according to the third embodiment.

FIG. 20 is an example of a magnetic meter. In the example shown in FIG. 20, the sensor part 301 is provided on a flat plate-shaped hard base 305.

In the example shown in FIG. 20, the input/output of the signal obtained from the sensor part 301 is the same as the input/output described with respect to FIG. 19. In the example shown in FIG. 20, the processing of the signal obtained from the sensor part 301 is the same as the processing described with respect to FIG. 19.

There is a reference example in which a SQUID (Superconducting Quantum Interference Device) magnetic sensor is used as a device for measuring a weak magnetic field such as a magnetic field generated from a living body. In this reference example, since superconductivity is used, the device is large and the power consumption is large. The burden on the measurement target (patient) is heavy.

According to the embodiment, the device can be miniaturized. Power consumption can be suppressed. The burden on the measurement target (patient) can be reduced. According to the embodiment, the SN ratio of magnetic field detection can be improved. Sensitivity can be improved.

The embodiment may include the following configurations (e.g., technical proposals).

(Configuration 1)

A magnetic sensor, comprising: a first sensor part, the first sensor part including, a first magnetic member;

a first counter magnetic member, a direction from the first magnetic member to the first counter magnetic member being along a first direction; and a first magnetic element including one or a plurality of first extending portions, a first portion of the first extending portion overlapping the first magnetic member in a second direction crossing the first direction, a first counter portion of the first extending portion overlapping the first counter magnetic member in the second direction, a first direction length along the first direction of the first extending portion being longer than a third direction length along a third direction of the first extending portion, the third direction crossing a plane including the first direction and the second direction.

(Configuration 2)

The Magnetic sensor according to Configuration 1, wherein the first magnetic element further includes a first electrode and a first counter electrode, the first electrode is electrically connected to the first portion, the first electrode overlaps the first magnetic member in the second direction, the first counter electrode is electrically connected to the first counter portion, and the first counter electrode overlaps the first counter magnetic member in the second direction.

(Configuration 3)

The magnetic sensor according to Configuration 2, wherein the first electrode and the first counter electrode do not overlap a region between the first magnetic member and the first counter magnetic member in the second direction.

(Configuration 4)

The magnetic sensor according to Configuration 2 or 3, wherein the plurality of first extending portions are provided, the plurality of first extending portions are arranged along the third direction, and the plurality of first extending portions are electrically connected in a meander shape.

(Configuration 5)

The magnetic sensor according to one of Configurations 2 to 4, wherein at least a part of the first portion is between the first magnetic member and the first electrode in the second direction, and at least a part of the first counter portion is between the first counter magnetic member and the first counter electrode in the second direction.

(Configuration 6)

The magnetic sensor according to one of Configurations 1 to 5, wherein the first portion includes apportion that does not overlap the first electrode in the second direction, and the first counter portion includes a portion that does not overlap the first counter electrode.

(Configuration 7)

The magnetic sensor according to one of Configurations 1 to 6, wherein an electric resistance of the first magnetic element has characteristics of an even function with respect to magnetic field applied to the first magnetic element.

(Configuration 8)

The magnetic sensor according to one of Configurations 1 to 7, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is higher than the second value and higher than the third value.

(Configuration 9)

The magnetic sensor according to one of Configurations 1 to 7, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is lower than the second value and lower than the third value.

(Configuration 10)

The magnetic sensor according to one of Configurations 1 to 9, wherein the first extending portion includes a first magnetic layer, a first counter magnetic layer, and a first nonmagnetic layer provided between the first magnetic layer and the first counter magnetic layer.

(Configuration 11)

The magnetic sensor according to Configuration 8, wherein the first extending portion includes a first magnetic layer including Co, a first counter magnetic layer including Co, and a first nonmagnetic layer including Cu, the first nonmagnetic layer being provided between the first magnetic layer and the first counter magnetic layer, the first magnetic layer includes a first magnetic region and a second magnetic region, the first magnetic region is between the first nonmagnetic layer and the second magnetic region, a concentration of Co in the first magnetic region is higher than a concentration of Co in the second magnetic region, the first counter magnetic layer includes a first counter magnetic region and a second counter magnetic region, the first counter magnetic region is between the first nonmagnetic layer and the second counter magnetic region, a concentration of Co in the first counter magnetic region is higher than a concentration of Co in the second counter magnetic region.

(Configuration 12)

The magnetic sensor according to Configuration 8 or 9, wherein the first extending portion includes a first magnetic layer, a first layer including at least one selected from the group consisting of IrMn and PtMn, a first counter magnetic layer provided between the first magnetic layer and the first layer, and a first nonmagnetic layer provided between the first magnetic layer and the first counter magnetic layer.

(Configuration 13)

The magnetic sensor according to Configuration 12, wherein the first extending portion includes a first magnetic film provided between the first counter magnetic layer and the first layer, and a first nonmagnetic film provided between the first counter magnetic layer and the first magnetic film.

(Configuration 14)

The magnetic sensor according to one of Configurations 1 to 13, wherein the first sensor part includes a first conductive member, at least a part of the first conductive member overlaps a region between the first magnetic member and the first counter magnetic member in the second direction, a first current including alternating current component is configured to flow through the first conductive member, and the first current is along the third direction.

(Configuration 15)

The magnetic sensor according to Configuration 14, further comprising:

a first current circuit configured to supply the first current to the first conductive member.

(Configuration 16)

The magnetic sensor according to one of Configurations 1 to 13, further comprising:

a second sensor part including a second magnetic element;

a third sensor part including a third magnetic element;

a fourth sensor part including a fourth magnetic element; and an element current circuit, one end of the first magnetic element being electrically connected to one end of the third magnetic element, an other end of the first magnetic element being electrically connected to one end of the second magnetic element, an other end of the third magnetic element being electrically connected to one end of the fourth magnetic element, an other end of the second magnetic element being electrically connected to an other end of the fourth magnetic element, the element current circuit being configured to supply an element current between a first connection point connecting the one end of the first magnetic element to the one end of the third magnetic element and a second connection point connecting the other end of the second magnetic element to the other end of the fourth magnetic element.

(Configuration 17)

The magnetic sensor according to Configuration 16, further comprising: a detection circuit, the detection circuit being configured to detect a change in a potential between a third connection point connecting the other end of the first magnetic element to the one end of the second magnetic element and a fourth connection point connecting the other end of the third magnetic element to the one end of the fourth magnetic element.

(Configuration 18)

The magnetic sensor according to Configuration 16 or 17, further comprising: a first current circuit, the first sensor part including a first conductive member, at least a part of the first conductive member overlapping a region between the first magnetic member and the first counter magnetic member in the second direction, the second sensor part including a second magnetic member, a second counter magnetic member, and a second conductive member, at least a part of the second conductive member overlapping a region between the second magnetic member and the second counter magnetic member in the second direction, the third sensor part including a third magnetic member, a third counter magnetic member, and a third conductive member, at least a part of the third conductive member overlapping a region between the third magnetic member and the third counter magnetic member in the second direction, the fourth sensor part including a fourth magnetic member, a fourth counter magnetic member, and a fourth conductive member, at least a part of the fourth conductive member overlapping a region between the fourth magnetic member and the fourth counter magnetic member in the second direction, one end of the first conductive member being electrically connected to one end of the third conductive member, an other end of the first conductive member being electrically connected to one end of the second conductive member, an other end of the third conductive member being electrically connected to one end of the fourth conductive member, an other end of the second conductive member being electrically connected to an other end of the fourth conductive member, the first current circuit being configured to supply a first current including alternating current between a fifth connection point connecting the other end of the first conductive member to the one end of the second conductive member and a sixth connection point connecting the other end of the third conductive member to the one end of the fourth conductive member.

(Configuration 19)

The magnetic sensor according to one of Configurations 1 to 18, wherein the first extending portion further includes a first intermediate portion between the first portion and the first counter portion, the first intermediate portion overlaps a region between the first magnetic member and the first counter magnetic member in the second direction, and a length along the third direction of the first intermediate portion is shorter than a length along the third direction of the first portion and shorter than a length along the third direction of the first counter portion.

(Configuration 20)

An inspection device, comprising:

the magnetic sensor according to one of Configurations 1 to 19; and a processor configured to process a signal output from the magnetic sensor.

According to the embodiments, a magnetic sensor and an inspection device which are possible to improve sensitivity can be provided.

In the specification of the application, “perpendicular” and “parallel” refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, nonmagnetic layers, magnetic members, conductive members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and Inspection devices practicable by an appropriate design modification by one skilled in the art based on the magnetic sensors, and the inspection devices described above as embodiments of the Invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising: a first sensor part, the first sensor part including, a first magnetic member;

a first counter magnetic member, a direction from the first magnetic member to the first counter magnetic member being along a first direction; and a first magnetic element including one or a plurality of first extending portions, a first portion of the first extending portion overlapping the first magnetic member in a second direction crossing the first direction, a first counter portion of the first extending portion overlapping the first counter magnetic member in the second direction, a first direction length along the first direction of the first extending portion being longer than a third direction length along a third direction of the first extending portion, the third direction crossing a plane including the first direction and the second direction, wherein the first sensor part includes a first conductive member, at least a part of the first conductive member overlaps a region between the first magnetic member and the first counter magnetic member in the second direction, a first current including alternating current component is configured to flow through the first conductive member, and the first current is along the third direction.

2. The magnetic sensor according to claim 1, wherein the first magnetic element further includes a first electrode and a first counter electrode, the first electrode is electrically connected to the first portion, the first electrode overlaps the first magnetic member in the second direction, the first counter electrode is electrically connected to the first counter portion, and the first counter electrode overlaps the first counter magnetic member in the second direction.

3. The magnetic sensor according to claim 2, wherein the first electrode and the first counter electrode do not overlap a region between the first magnetic member and the first counter magnetic member in the second direction.

4. The magnetic sensor according to claim 2, wherein the plurality of first extending portions are provided, the plurality of first extending portions are arranged along the third direction, and the plurality of first extending portions are electrically connected in a meander shape.

5. The magnetic sensor according to claim 2, wherein at least a part of the first portion is between the first magnetic member and the first electrode in the second direction, and at least a part of the first counter portion is between the first counter magnetic member and the first counter electrode in the second direction.

6. The magnetic sensor according to claim 2, wherein the first portion includes a portion that does not overlap the first electrode in the second direction, and the first counter portion includes a portion that does not overlap the first counter electrode.

7. The magnetic sensor according to claim 1, wherein an electric resistance of the first magnetic element has characteristics of an even function with respect to magnetic field applied to the first magnetic element.

8. The magnetic sensor according to claim 1, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is higher than the second value and higher than the third value.

9. The magnetic sensor according to claim 8, wherein the first extending portion includes a first magnetic layer including Co, a first counter magnetic layer including Co, and a first nonmagnetic layer including Cu, the first nonmagnetic layer being provided between the first magnetic layer and the first counter magnetic layer, the first magnetic layer includes a first magnetic region and a second magnetic region, the first magnetic region is between the first nonmagnetic layer and the second magnetic region, a concentration of Co in the first magnetic region is higher than a concentration of Co in the second magnetic region, the first counter magnetic layer includes a first counter magnetic region and a second counter magnetic region, the first counter magnetic region is between the first nonmagnetic layer and the second counter magnetic region, a concentration of Co in the first counter magnetic region is higher than a concentration of Co in the second counter magnetic region.

10. The magnetic sensor according to claim 8, wherein the first extending portion includes a first magnetic layer, a first layer including at least one selected from the group consisting of IrMn and PtMn, a first counter magnetic layer provided between the first magnetic layer and the first layer, and a first nonmagnetic layer provided between the first magnetic layer and the first counter magnetic layer.

11. The magnetic sensor according to claim 10, wherein the first extending portion includes a first magnetic film provided between the first counter magnetic layer and the first layer, and a first nonmagnetic film provided between the first counter magnetic layer and the first magnetic film.

12. The magnetic sensor according to claim 1, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is lower than the second value and lower than the third value.

13. The magnetic sensor according to claim 1, wherein the first extending portion includes a first magnetic layer, a first counter magnetic layer, and a first nonmagnetic layer provided between the first magnetic layer and the first counter magnetic layer.

14. The magnetic sensor according to claim 1, further comprising:

a first current circuit configured to supply the first current to the first conductive member.

15. The magnetic sensor according to claim 1, wherein the first extending portion further includes a first intermediate portion between the first portion and the first counter portion, the first intermediate portion overlaps a region between the first magnetic member and the first counter magnetic member in the second direction, and a length along the third direction of the first intermediate portion is shorter than a length along the third direction of the first portion and shorter than a length along the third direction of the first counter portion.

16. An inspection device, comprising:

the magnetic sensor according to claim 1; and a processor configured to process a signal output from the magnetic sensor.

17. A magnetic sensor, comprising: a first sensor part, the first sensor part including, a first magnetic member;

a first counter magnetic member, a direction from the first magnetic member to the first counter magnetic member being along a first direction; and a first magnetic element including one or a plurality of first extending portions, a first portion of the first extending portion overlapping the first magnetic member in a second direction crossing the first direction, a first counter portion of the first extending portion overlapping the first counter magnetic member in the second direction, a first direction length along the first direction of the first extending portion being longer than a third direction length along a third direction of the first extending portion, the third direction crossing a plane including the first direction and the second direction, the first magnetic element further including a first electrode and a first counter electrode, a first distance between the first electrode and the first counter electrode being greater than or equal to a second distance between the first magnetic member and the first counter magnetic member, and the first direction length being longer than the second distance.

18. The magnetic sensor according to claim 17, further comprising:

a second sensor part including a second magnetic element;

a third sensor part including a third magnetic element;

a fourth sensor part including a fourth magnetic element; and an element current circuit, one end of the first magnetic element being electrically connected to one end of the third magnetic element, an other end of the first magnetic element being electrically connected to one end of the second magnetic element, an other end of the third magnetic element being electrically connected to one end of the fourth magnetic element, an other end of the second magnetic element being electrically connected to an other end of the fourth magnetic element, the element current circuit being configured to supply an element current between a first connection point connecting the one end of the first magnetic element to the one end of the third magnetic element and a second connection point connecting the other end of the second magnetic element to the other end of the fourth magnetic element.

19. The magnetic sensor according to claim 18, further comprising: a detection circuit, the detection circuit being configured to detect a change in a potential between a third connection point connecting the other end of the first magnetic element to the one end of the second magnetic element and a fourth connection point connecting the other end of the third magnetic element to the one end of the fourth magnetic element.

20. The magnetic sensor according to claim 18, further comprising: a first current circuit, the first sensor part including a first conductive member, at least a part of the first conductive member overlapping a region between the first magnetic member and the first counter magnetic member in the second direction, the second sensor part including a second magnetic member, a second counter magnetic member, and a second conductive member, at least a part of the second conductive member overlapping a region between the second magnetic member and the second counter magnetic member in the second direction, the third sensor part including a third magnetic member, a third counter magnetic member, and a third conductive member, at least a part of the third conductive member overlapping a region between the third magnetic member and the third counter magnetic member in the second direction, the fourth sensor part including a fourth magnetic member, a fourth counter magnetic member, and a fourth conductive member, at least a part of the fourth conductive member overlapping a region between the fourth magnetic member and the fourth counter magnetic member in the second direction, one end of the first conductive member being electrically connected to one end of the third conductive member, an other end of the first conductive member being electrically connected to one end of the second conductive member, an other end of the third conductive member being electrically connected to one end of the fourth conductive member, an other end of the second conductive member being electrically connected to an other end of the fourth conductive member, the first current circuit being configured to supply a first current including alternating current between a fifth connection point connecting the other end of the first conductive member to the one end of the second conductive member and a sixth connection point connecting the other end of the third conductive member to the one end of the fourth conductive member.

* * * * *